(12) United States Patent
Harrison et al.

(10) Patent No.: US 11,844,629 B2
(45) Date of Patent: Dec. 19, 2023

(54) MRI TRANSPORTER APPARATUS AND METHODS

(71) Applicant: SYNAPTIVE MEDICAL INC., Toronto (CA)

(72) Inventors: Dan Gavin Harrison, Toronto (CA); Mark Tullio Morreale, Toronto (CA); William Wai-Leung Lau, Toronto (CA); Murtasim Syed, Toronto (CA); Genevieve Rodrigue, Toronto (CA); Aryeh Benjamin Taub, Toronto (CA)

(73) Assignee: Synaptive Medical Inc.

( * ) Notice: Subject to any disclaimer, the term of this patent is extended or adjusted under 35 U.S.C. 154(b) by 201 days.

(21) Appl. No.: 17/305,679

(22) Filed: Jul. 13, 2021

(65) Prior Publication Data

US 2022/0008016 A1 Jan. 13, 2022

Related U.S. Application Data

(60) Provisional application No. 63/050,889, filed on Jul. 13, 2020.

(51) Int. Cl.
| | |
|---|---|
| A61B 5/00 | (2006.01) |
| A61B 5/055 | (2006.01) |
| A61G 3/00 | (2006.01) |
| A61G 99/00 | (2006.01) |

(52) U.S. Cl.
CPC .............. *A61B 5/70* (2013.01); *A61B 5/055* (2013.01); *A61G 3/001* (2013.01); *A61G 99/00* (2013.01); *A61B 2560/0456* (2013.01); *A61G 2203/14* (2013.01); *A61G 2203/22* (2013.01); *A61G 2203/30* (2013.01); *A61G 2210/30* (2013.01)

(58) Field of Classification Search
CPC .......... A61B 5/70; A61B 5/055; A61G 3/001; A61G 99/00; A61G 2203/14; A61G 2203/22; A61G 2203/30
See application file for complete search history.

(56) References Cited

U.S. PATENT DOCUMENTS

| | | | |
|---|---|---|---|
| 6,776,527 B1 * | 8/2004 | Tybinkowski | A61B 6/04 378/209 |
| 2006/0167356 A1 * | 7/2006 | Everett | A61B 6/0487 600/407 |
| 2021/0068701 A1 * | 3/2021 | Piron | A61B 5/0036 |

\* cited by examiner

*Primary Examiner* — Joel F Brutus

(57) ABSTRACT

A smart system and methods for coupling a medical transporter apparatus with an imaging apparatus, involving: a smart docking module comprising at least one coupler responsive to a controller operable by a set of executable instructions, the smart docking module comprising a non-magnetic material; and the smart docking module configured by the controller to automatically perform at least one of: position, dock, engage, latch, lock, interlock, release, emergency-release, quick-release, disengage, emergency-disengage, and quick-disengage the medical transporter apparatus in relation to the imaging apparatus.

17 Claims, 29 Drawing Sheets

| Name | Brief Desc. | Purpose | Outcome | Notes |
|---|---|---|---|---|
| INF-A | Dock Status (Dock- BT Interlock) | Communicates if dock is fully engaged. | Permits the bed top to slide when the PT is fully docked. | Cable driven cam lock actuated by the action of fully docking the PT. |
| INF-B | Height Status (Height-BT Interlock) | Communicates if stretcher is at scanning height. | Permits the bed top to slide when the PT is at the scanning height. | Cable driven cam lock actuated by the action of the PT hitting it's maximum height |
| INF-C | Dock Status | Communicates dock status to scanner | Is PT docked to scanner (Yes/No) | Photointerruptor on scanner which is triggered by a flag on the PT when the PT is docked |
| INF-D | Service/Emergency Undock Engaged | Communicates status of service undock to user | If service undock has been actuated the docking feature of the stretcher should be disabled (therefore disabling the bed top). This will prevent further use of the docking module (and therefore the scanner) until the service undock has been reset. | Ideally actuation of the service/emergency undock will passivate or lock the docking pedals to provide clear tactile feedback that the dock is not usable. |
| INF-E | Caster Status | Communicates status of caster lock to user | Provide visual feedback to user on status of casters. | Not critical to operation – not an interlock. |
| INF-F | Dock Status | Communicates status of dock to user | Provide visual feedback to user on status of casters. | Not critical to operation – not an interlock |
| INF-G | Service Undock Status | Communicates status of service undock to user | Provide tactile feedback to user if service undock has been used. | Actuation of service undock should passivate dock pedal. Resetting the service undock should reactivate the dock pedals. |
| INF-H | BT Status, Dock (BT, Dock Interlock) | Communicates states of bed top to dock | Prevents PT from undocking until the BT is in the transport position | Lever/cable mechanism that physically prevents undocking when BT is extended |
| INF-J | Bed Top Status - Height (BT-Height Interlock) | Communicates states of bed top to height pedal | Prevents PT from undocking until the BT is in the transport position | Lever/cable mechanism that physically prevents undocking when BT is extended |
| INF-K | Bed Top Status - Height | Communicates status of BT to scanner | Is BT at scanning Height (Yes/No) | Photointerruptor on scanner which is triggered when the PT is at scanning height |

FIG. 10B

| Name | Brief Desc. | Purpose | Outcome | Notes |
|---|---|---|---|---|
| MECH-A | Dock Actuation | Two distinct pedals that engage and disengage the dock. | | Requires User Input |
| MECH-B | Height Adjustment | One pedal that raises the PT bed with a downward pumping motion, or lowers it by lifting the pedal. | | Requires User Input |
| MECH-C | Caster lock | Two pedals that allow the casters to be centrally brake-locked, swivel- locked, or totally unlocked | | Requires User Input |
| MECH-D | Passivate Latch | Automatically disengages the latch as the dock is disengaged | | Driven by MECH-A – requires no separate user input |
| MECH-E | Height Latch / Unlatch | Automatically activates at right height | Not required - the latch status is Irrelevant unless the PT is at a height where the PP can attach | Driven by MECH-A – requires no separate user input |
| MECH-F | PP Latch | Mechanical latch that couples the Z-axis motion of the patient positioner to the bed top | | Should automatically engage when PP approaches the BT. Disengagement will occur with actuation of MECH-D, or MECH-G |
| MECH-G | Manual Unlatch | Mechanical decoupling of the latch actuated from the foot of the BT. | | Question: will actuation of the manual unlatch passivate further latch engagement until a separate user intervention? |
| MECH-H | Secondary Undock | Mechanical decoupling of the PT from the scanner | | Actuated from near the docking module. Not intended for regular use – only to be used in the event of a failure to undock through MECH-A. After actuation of service undock, MECH-A will be passivated until further intervention (i.e. docking mechanism will need to be "reset") |

FIG. 10C

MRI TRANSPORTER APPARATUS AND METHODS

CROSS REFERENCE TO RELATED APPLICATION

The application claims priority and the benefit of U.S. Provisional Patent Application Ser. No. 63/050,889, entitled "MM TRANSPORTER APPARATUS AND METHODS", filed on Jul. 13, 2020, the disclosure of which is incorporated herein by reference in its entirety.

TECHNICAL FIELD

Generally, the present disclosure technically relates to patient transport apparatuses and methods. More particularly, the present disclosure technically relates to patient transport apparatuses and methods for use with MRI machines. Even more particularly, the present disclosure technically relates to patient transport apparatuses and methods that are interfaceable with MRI machines.

BACKGROUND

In the related art, various patient transporters have been used for performing a variety of medical procedures. For example, a related art modular intervention bed has been used with a medical tomographic imaging system, the bed having an associated patient transport device and an imaging device. The modular intervention bed has a trestle configured to engage a patient transport device, with the trestle having an intervention area. A patient couch movably mounted on the trestle, with the patient couch defining an opening corresponding to the intervention area. The couch has a plurality of patient mats with each mat connected to at least one other mat, a pair of rollers mounted on each mat in a spaced apart relationship with each roller proximate an outside edge of each mat. The modular intervention bed can be reconfigured by adding or removing a mat, thereby moving the intervention area and opening to correspond with the portion of a patient under investigation during an intervention procedure guided by a medical tomographic imaging system. However, this related art modular intervention bed merely uses rollers and does not have any features for safely interfacing and interlocking with the medical tomographic imaging system.

Another related art apparatus involves a patient support apparatus used with navigation and guidance systems and has control systems with one or more image, radar, and/or laser sensors to detect objects and determine if a likelihood of collision exists, wherein the control system controls the speed and steering of the patient support apparatus to reduce the likelihood of collision. The control system may be adapted to autonomously drive the patient support apparatus, to transmit a message to a remote device indicating whether it is occupied by a patient or not, and/or to transmit its route to the remote device. The remote device may determine an estimate of a time of arrival of the patient support apparatus at a particular destination and/or determine a distance of the patient support apparatus from the particular destination. However, this related art patient support apparatus does not have features for safely interfacing and interlocking with an MRI machine. Rather, this related art patient support apparatus uses materials that are incompatible with MRI and is configured for only patient transport within a hospital.

Yet another related art system involves a patient positioning system for use with an imaging system, wherein a palette for an imaging system is provided that includes a base portion movably connected to the imaging system and an extender portion removably connected to the base portion. The extender portion together with the base portion supports an object to be imaged by the imaging system. However, this related art patient positioning system also merely uses rollers and does not have any features for safely interfacing and interlocking with the imaging system.

Yet still another related art system involves a transport bed having a lifting mechanism, a bed body, and a table base, wherein the bed body and the table base are connected through the lifting mechanism. A controlling device is arranged on the base seat of the table base. At least two cross beams are arranged on the bed frame, the position corresponding with the cross beams of the backside of the bed board is provided with a smooth sliding face which is beneficial for the bed board to slide left and right along the cross beams. Two sides of the bed frame are movably provided with protecting boards used for fixing the bed board. When the bed board moves on the cross beams of the bed frame, due to the fact a friction factor is quite small, medical staff can move the bed board to medical equipment. The bedframe has antimagnetic materials. However, this related art transport bed also merely uses rollers and does not have any features for safely interfacing and interlocking with an imaging system.

Yet still another related art system involves a patient bed for use with an NMR imaging system. An expanded diagnostic NMR installation with operating functionality contains an NMR imaging apparatus with a patient bed for transporting a patient into an imaging volume of the NMR imaging apparatus. An operating column for receiving the patient bed is arranged next to the NMR imaging apparatus at a fixed distance therefrom along the longitudinal direction of motion of the patient bed. The operating column contains a swinging mechanism for rotating or pivoting the patient bed around a vertical axis. However, this related art transport bed merely docks with an operating column and does not have any features for safely interfacing and interlocking with an imaging system.

Therefore, a need exists in the related art, for a mechanical transport system that can move a patient from an intensive care unit (ICU) to a magnetic resonance imaging (MRI) machine without having to lift the patient from one surface to another surface, e.g., that eliminates a need for transferring patient from one type of medical bed to another type of medical bed, and that facilitates quickly scanning a patient.

SUMMARY

The present disclosure addresses at least many of the foregoing challenges experienced by related art. The subject matter of the present disclosure involves a transporter apparatus and methods that facilitate moving a patient from an intensive care unit (ICU) to a magnetic resonance imaging (MRI) machine without having to lift the patient from one surface to another surface, e.g., that eliminates a need for transferring patient from one type of medical bed to via a safer docking-and-undocking mechanism. The docking-and-undocking mechanism comprises: at least a five-way interlocking feature configured to quick-connect and quick disconnect in relation to an MRI machine and an MRI head coil; and a sensor system for safety detection.

In accordance with an embodiment of the present disclosure, a smart system for coupling a medical transporter apparatus with an imaging apparatus, comprises: a smart docking module comprising at least one coupler responsive to a controller operable by a set of executable instructions, the smart docking module comprising a non-magnetic material; and the smart docking module configured by the controller to automatically perform at least one of: position, dock, engage, latch, lock, interlock, release, emergency-release, quick-release, disengage, emergency-disengage, and quick-disengage the medical transporter apparatus in relation to the imaging apparatus.

In accordance with another embodiment of the present disclosure, a method of fabricating a smart system for coupling a medical transporter apparatus with an imaging apparatus, comprising: providing a smart docking module comprising providing at least one coupler responsive to a controller operable by a set of executable instructions, providing the smart docking module comprising providing a non-magnetic material; and providing the smart docking module comprising configuring the smart docking module, by the controller, to automatically perform at least one of: position, dock, engage, latch, lock, interlock, release, emergency-release, quick-release, disengage, emergency-disengage, and quick-disengage the medical transporter apparatus in relation to the imaging apparatus.

In accordance with another embodiment of the present disclosure, a method of for coupling a medical transporter apparatus with an imaging apparatus by way of a smart system, comprising: providing the smart system, providing the smart system comprising: providing a smart docking module comprising providing at least one coupler responsive to a controller operable by a set of executable instructions, providing the smart docking module comprising providing a non-magnetic material; and providing the smart docking module comprising configuring the smart docking module, by the controller, to automatically perform at least one of: position, dock, engage, latch, lock, interlock, release, emergency-release, quick-release, disengage, emergency-disengage, and quick-disengage the medical transporter apparatus in relation to the imaging apparatus; and activating the smart system, thereby automatically docking the medical transporter apparatus with the imaging apparatus.

Some of the features in the present disclosure are broadly outlined in order that the section entitled Detailed Description is better understood and that the present contribution to the art may be better appreciated. Additional features of the present disclosure are described hereinafter. In this respect, understood is that the present disclosure is not limited in its application to the details of the components or steps set forth herein or as illustrated in the several figures of the being carried out in various ways. Also, understood is that the phraseology and terminology employed herein are for the purpose of the description and should not be regarded as limiting.

BRIEF DESCRIPTION OF THE DRAWING

The above, and other, aspects, features, and advantages of several embodiments of the present disclosure will be more apparent from the following Detailed Description as presented in conjunction with the following several figures of the Drawing.

FIGS. 10B and 10C are tables containing a brief description of the steps in the method of interfacing a medical transporter apparatus with an imaging apparatus, by way of a smart system, using the plurality of interlocks, as shown in FIG. 10A, in accordance with embodiments of the present disclosure.

FIGS. 12C and 12D are diagrams illustrating respective partial views of the bed respectively interlocked and released for adjusting elevation relative to the base by way of an interlocking foot pedal system, in accordance with an embodiment of the present disclosure.

Figure 1A:
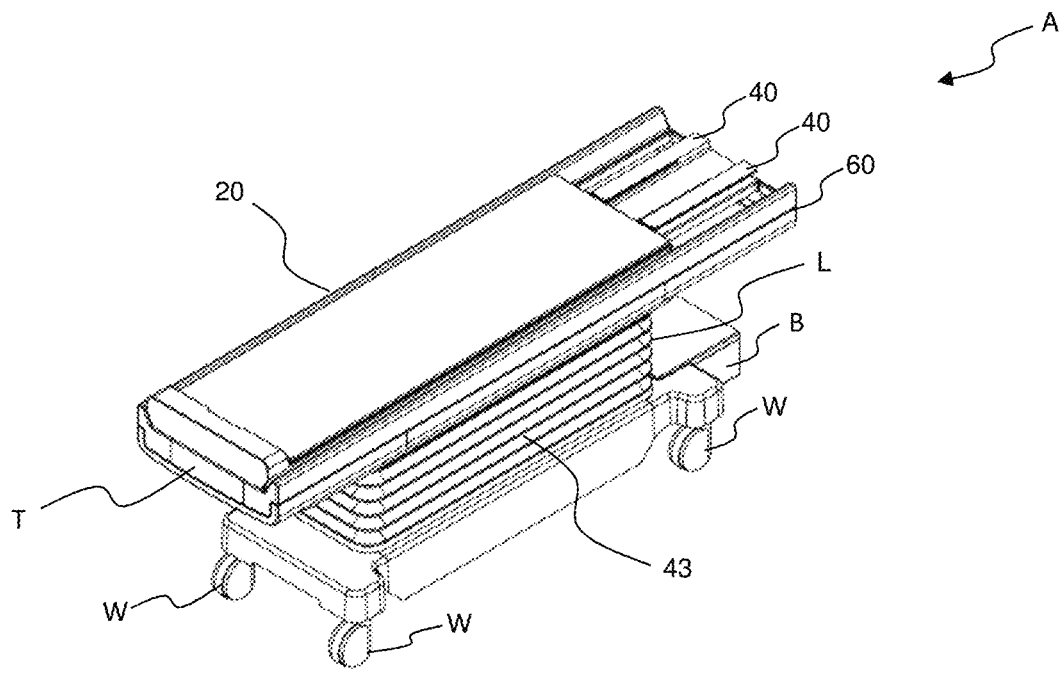
FIG. 1A is a diagram illustrating a perspective view of a patient transporter (PT) or a medical transporter apparatus, such as an MRI transporter, adaptable for operation by a smart system, the smart system comprising a smart docking module, in accordance with an embodiment of the present disclosure.

Corresponding reference numerals or characters indicate corresponding components throughout the several figures of the Drawing. Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood, elements that are useful or necessary in commercially feasible embodiment are often not depicted in order to facilitate a less obstructed view of these various embodiments of the present disclosure.

DETAILED DESCRIPTION

Figure 5:
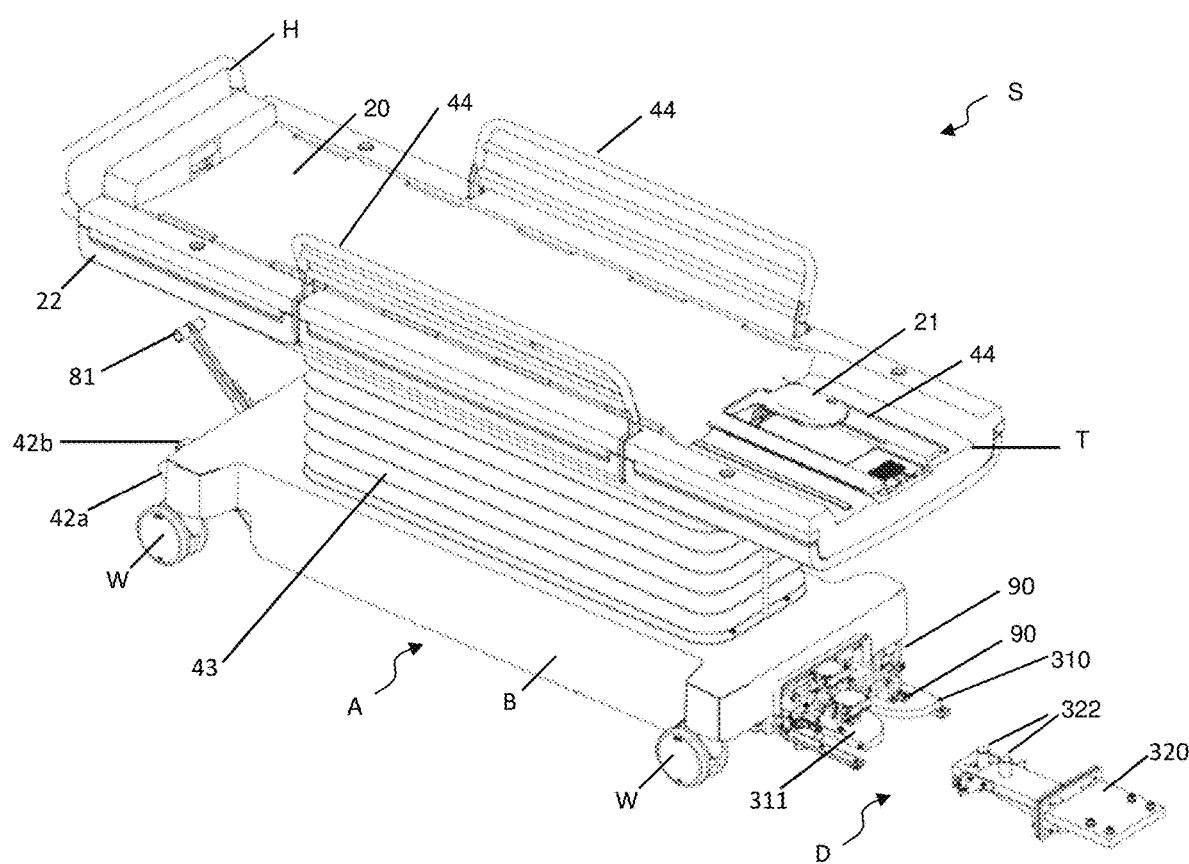
FIG. 5 is a diagram illustrating a perspective view of a smart system, comprising a medical transporter apparatus and a smart docking module, wherein a table comprises a handle, wherein a bed or bed top (BT) comprises a tongue portion, wherein the smart docking module comprises an active docking module and a passive docking module, wherein the passive docking module is configured to couple with a receiver portion of an imaging apparatus, and wherein the bed disposed in a highest elevation, in accordance with an embodiment of the present disclosure.

Referring to FIG. 1A, this diagram illustrates, in a perspective view, a PT or a medical transporter apparatus A, such as an MRI transporter, adaptable for operation by a smart system S, the smart system S comprising a smart docking module D (FIG. 2A), in accordance with an embodiment of the present disclosure. Components of the smart system S are disposable within at least one of a base B, a table T, and a lift portion L of the medical transporter apparatus A. The smart system S is configured to couple the medical transporter apparatus A with medical equipment, such as an imaging apparatus I, e.g., an MRI machine (FIG. 1B), by way of a smart docking module D. The smart docking module D comprises a non-magnetic material and at least one coupler (FIG. 5).

Still referring to FIG. 1A, the smart docking module D is responsive to a controller (not shown) operable by a set of executable instructions; and the smart docking module D is configured by a controller (not shown) to automatically perform at least one of: position, dock, engage, latch, lock, interlock, release, emergency-release, quick-release, disengage, emergency-disengage, and quick-disengage the medical transporter apparatus A in relation to medical equipment, such as the imaging apparatus I. The controller comprises at least one of: a computer, a processor, a processing unit, a power source, a memory device, and a safety device. The at least one coupler comprises at least one latch. The controller is disposed in relation to the system S, either wired or wirelessly; and, alternatively, the controller is remotely disposed. Alternatively, the smart docking module is manually or mechanically operable in the absence of a controller.

Figure 2A:
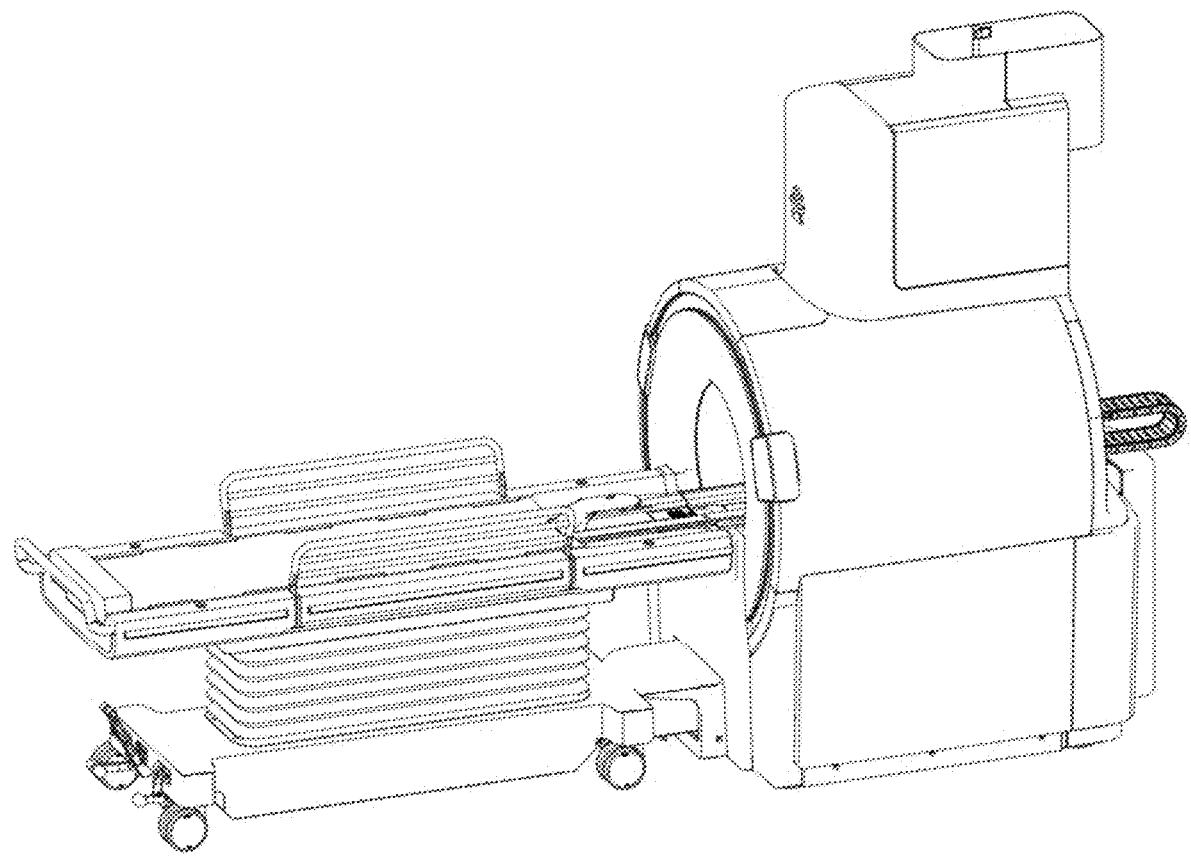
FIG. 2A is a diagram illustrating a perspective view of a smart system for coupling a medical transporter apparatus with an imaging apparatus, in accordance with an embodiment of the present disclosure.
Figure 2B:
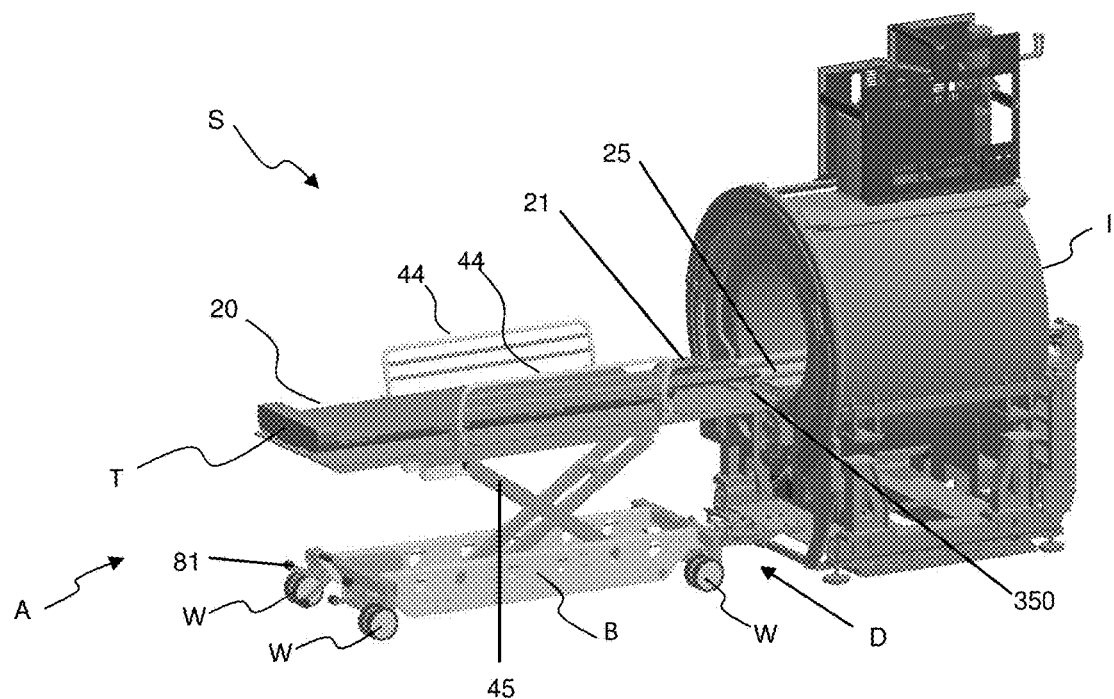
FIG. 2B is a diagram illustrating a cross-sectional perspective view of the smart system for coupling the medical transporter apparatus with the imaging apparatus, as shown in FIG. 2A, in accordance with an embodiment of the present disclosure.

Still referring to FIG. 1A, the smart system S may further comprise the medical transporter apparatus A itself as well, wherein the medical transporter apparatus A comprises: a table T, a bed 20, a base B having at least one wheel W; and a lift portion L, the lift portion L coupling the table T with the base B, and the lift portion L configured to adjust elevation of the table T in relation to the base B. The system S further comprises a deployment mechanism having a motor-and-rail system 40 for facilitating at least one of: deployment of the bed 20 from the table T and into a scanning volume $V_s$ of the imaging apparatus I; return of the bed 20 from the scanning volume $V_s$ of the imaging apparatus I to the table T; deployment of an active docking module 310 (FIG. 5) of the smart docking module D from the base B to a passive docking module 320 (FIG. 5) coupled with a receiver portion R (FIG. 7B) of the imaging apparatus I; and return of active docking module 310 of the smart docking module D to the base B from the passive docking module 320 coupled with the receiver portion R of the imaging apparatus I; and a self-positioning mechanism for automatically aligning the bed 20 with the scanning volume $V_s$ of the imaging apparatus I and the at least one smart coupler, e.g., the latching mechanism 350 (FIG. 7A) with the patient positioner 25 of the imaging apparatus I in at least one orthogonal direction (FIGS. 2A and 2B). The bed 20 further comprises a tongue portion 21 (FIGS. 4A and 4B) configured to interface with an MRI head coil (not shown) of the imaging apparatus I. The lift portion L comprises a housing 43 and a lifting mechanism 45 (FIGS. 2A and 2B). The housing 43 comprises a bellows configuration, by example only.

Figure 1B:
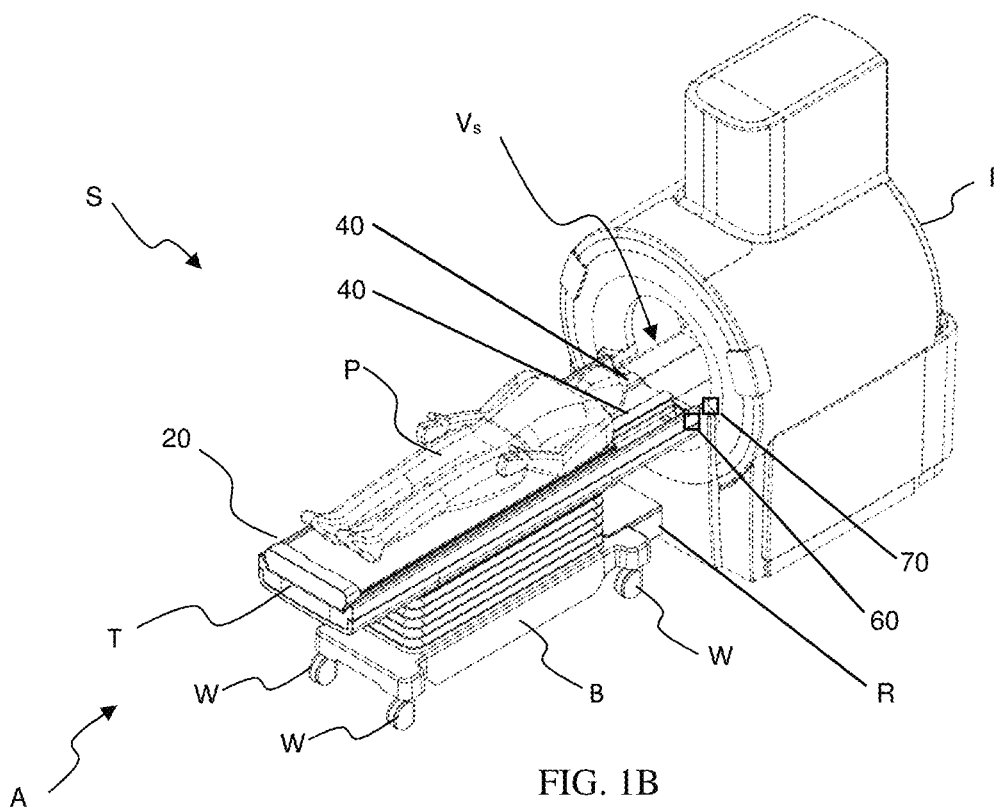
FIG. 1B is a diagram illustrating a perspective view of the medical transporter apparatus, such as an MRI transporter, as included in the smart system, as shown in FIG. 1B, docked in relation to a piece of medical equipment, such as an imaging apparatus, in accordance with an embodiment of the present disclosure.
Figure 3A:
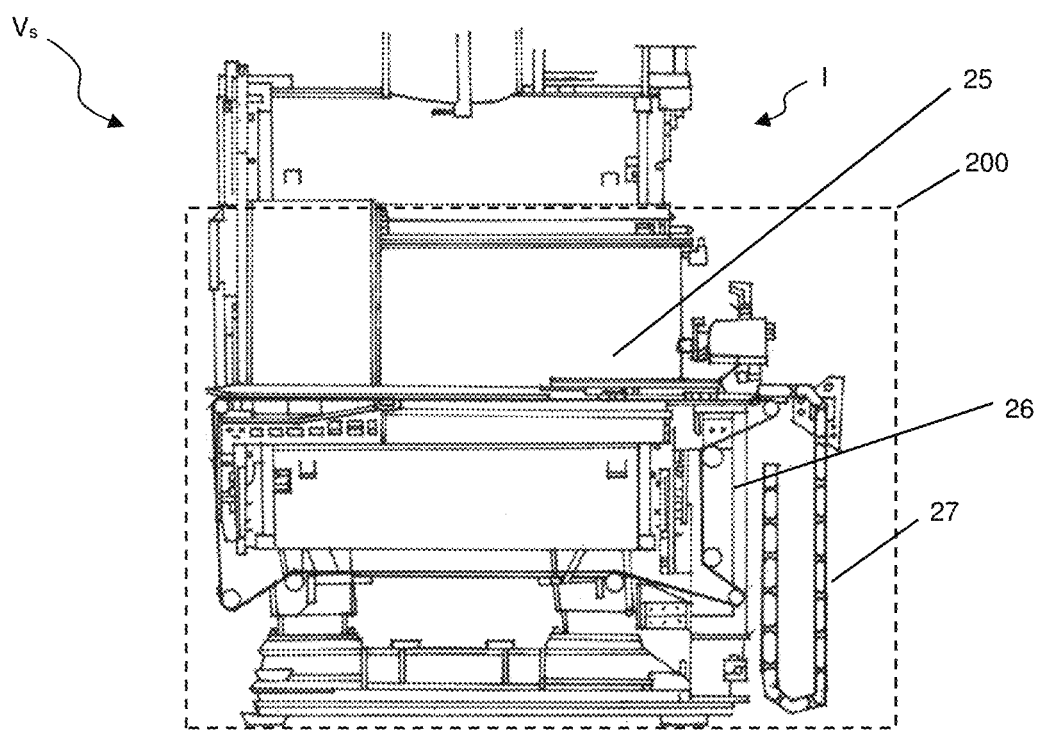
FIG. 3A is a diagram illustrating a cross-sectional side view of the imaging apparatus, as shown in FIGS. 2A, 2B and 2C, the imaging apparatus comprising a patient positioner and a motion system having a belt drive system, with which a smart system is implementable, in accordance with embodiments of the present disclosure.

Still referring to FIG. 1A and ahead to FIG. 1B, the smart system S further comprises: at least one indicator 60 disposable in relation to the medical transporter apparatus A and configured to indicate a real-time position of the medical transporter apparatus A; and at least one detector 70 disposable in relation to the imaging apparatus I and configured to detect the at least one indicator 60. The at least one indicator 60 comprises at least one of: at least one tracking marker, at least one fluorescent tracking marker, and at least one infrared tracking marker. The at least one detector 70 comprises at least one of: at least one sensor, at least one optical sensor, at least one photo-sensor, at least one photo-detector, at least one electric eye, at least one infrared sensor, and at least one photo-interrupter. The smart system S further comprises: a user interface, the user interface comprising at least one of: a foot pedal, e.g., a foot pedal 81 (FIGS. 4A and 4B), a handle, e.g., a handle H (FIG. 5), a joystick, and a graphic user interface, the user interface 80 facilitating at least one of activation, control and manual override of at least one of: the at least one coupler, the deployment mechanism 30, and the self-positioning mechanism. The self-positioning mechanism comprises at least one of: a patient positioner 25 (FIG. 8A), a belt-drive system 26 (FIGS. 3A and 3B), and a cable carrier system 27 (FIG. 3A).

Referring to FIG. 1B, this diagram illustrates, in a perspective view, the medical transporter apparatus A, such as an MRI transporter, as included in the smart system S, as shown in FIG. 1B, docked in relation to a piece of medical equipment, such as the imaging apparatus I, in accordance with an embodiment of the present disclosure. The smart docking module D of the system S is configured to effect interfacing the medical transporter apparatus A with at least one piece of medical equipment, such as the imaging apparatus I, e.g., an MRI machine. The smart docking module D is further configured to effect interfacing the tongue portion 21 (FIGS. 4A and 4B) with the MRI head coil (not shown) of the imaging apparatus I. The bed 20 is configured to accommodate a patient P and comprises at least one of: a magnetic resonance imaging table, a surgery table, a cart, a bed, a frame, a mattress, a gurney, and a stretcher, by example only. The medical transporter apparatus A comprises any other type of patient support or transporter for any type of medical procedure, wherein the smart system is reconfigurable for any particular type of medical equipment. The imaging apparatus I comprises at least one of a magnetic resonance imaging machine, a magnetic resonance angiography machine, a nuclear magnetic resonance machine, and any other type of magnetic imaging machine.

Still referring to FIG. 1B, an implementation example of the system S involves manually moving or automatically moving, such as by self-transporting via robotics, the medical transporter apparatus A to the imaging apparatus I; docking the medical transporter apparatus A with the imaging apparatus I, aligning the medical transporter apparatus A with the imaging apparatus I, and locking the medical transporter apparatus A with the imaging apparatus I, thereby securing to the medical transporter apparatus A with the imaging apparatus I. Further, the bed 20 is configured to translate or slide in relation to the table T of the medical transporter apparatus A, whereby any need for transferring the patient P from a stretcher (not shown) to a scanning bed (not shown) is eliminated. Also, the system S further comprises the controller, such as at least one processor (not shown) and at least one actuator or mechanism (FIGS. 10A and 10B) that are disposable in relation to any component of the medical transporter apparatus A, wherein the at least one processor and the at least one actuator are operable by way of a set of executable instructions. Such instructions include but are not limned to, an instruction for preventing the bed 20 from translating in relation to the table T toward the scanning volume $V_s$ of the imaging apparatus I until the table T is fully docked at the desired elevation and the base B is locked with the receiver portion R of the imaging apparatus I, such as by way of an interlocking feature, e.g., the smart docking module D (FIGS. 5 and 6A-6D), and an instruction for preventing undocking the medical transporter apparatus A from the imaging apparatus I until the bed 20 has fully translated back to its original position in relation to the table T, whereby patient safety and equipment safety are improvable.

Figure 8A:
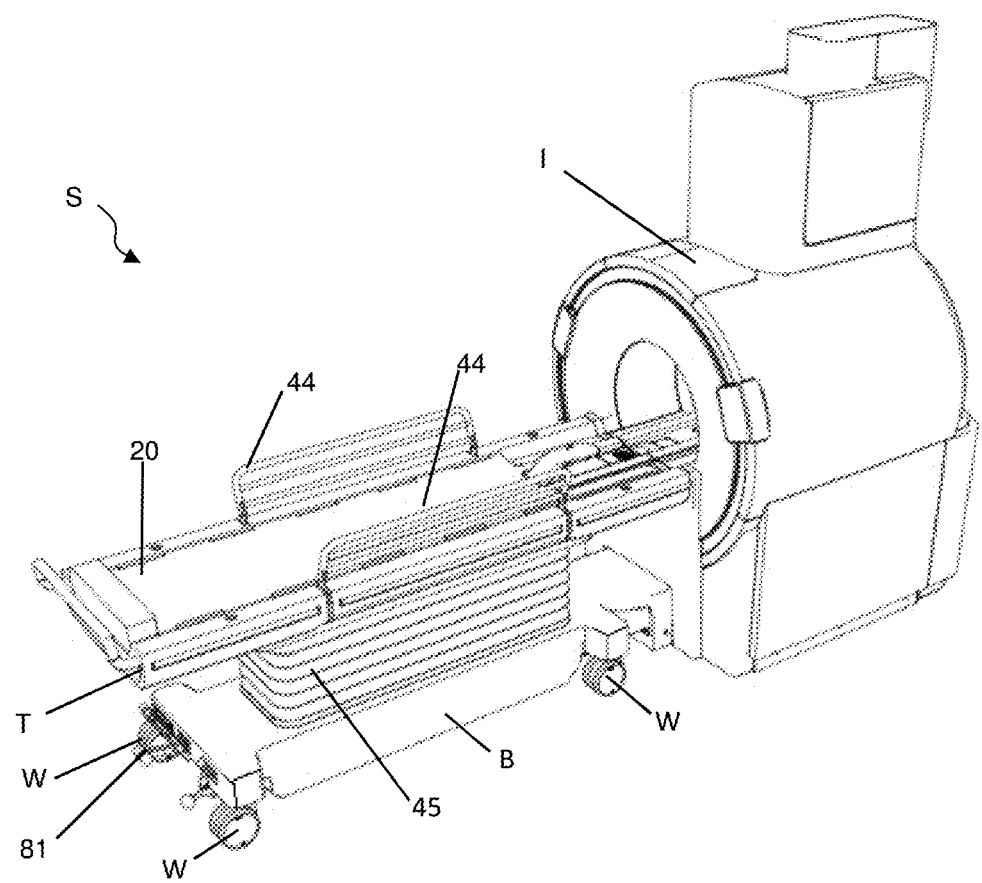
FIG. 8A is a diagram illustrating a perspective view of a smart system comprising a medical transporter apparatus and a smart docking module, wherein the medical transporter apparatus is docked with the imaging apparatus, wherein the medical transporter apparatus is disposed at any height, wherein the bed is disposed in a "transport" position, in accordance with an embodiment of the present disclosure.

Still referring to FIG. 1B, another implementation example of the system S involves manually moving the medical transporter apparatus A to the imaging apparatus I; approximately manually aligning the medical transporter apparatus A with the imaging apparatus I, and activating the smart docking module D, wherein the self-positioning mechanism, e.g., the patient positioner 25 (FIG. 8A), automatically aligns the bed 20 with the scanning volume $V_s$ of the imaging apparatus I and the at least one smart coupler, e.g., the active docking module 310 with the passive docking module 320 coupled with the receiver portion R of the imaging apparatus I in at least one orthogonal direction (FIG. 8A). In this embodiment, activating the smart docking module D is effected by a user actuating a docking interface pedal system, e.g., the pedal system 370 (FIG. 12), whereby the medical transporter apparatus A is moved into a docking position in relation to the imaging apparatus I, whereby the medical transporter apparatus A is aligned and locked, whereby an interlocking feature, e.g., the latching mechanism 350, releases the bed 20, and whereby the bed 20 is movable, e.g., translatable in relation to the table T, e.g., via the motor-and-rail system 40.

Still referring to FIG. 1B, the medical transporter apparatus A is aligned and locked (both conditions satisfied), detectors, such as a plurality of sensors, e.g., two sensors, disposed in relation to the imaging apparatus I are activated by indicators, e.g., flags, disposed in relation to the medical transporter apparatus A, whereby movement of the table T and the base B of the medical transporter apparatus A is prevented. Once the imaging apparatus I recognizes, via the plurality of sensors, that the table T is docked at the proper elevation and that the base B is locked, a processor (not shown) of the imaging apparatus I effects transmission of a message or prompt indicating that the imaging apparatus I is ready for imaging or scanning. Subsequently, the motor-and-rail system 40 is activated and moves the bed 20 into the scanning volume $V_s$ of the imaging apparatus I, whereby the tongue portion 21 engages with a head coil. After imaging or scanning, the smart docking module D instructs and/or effects actuation of the motor-and-rail system 40 to move the bed 20 from the scanning volume $V_s$ of the imaging apparatus I and to the bed's original position in relation to the table T of the apparatus A. Thereafter, the smart docking module D instructs the active docking module 310 to disengage from the passive docking module 320 coupled with the receiver portion R of the imaging apparatus I, thereby undocking the apparatus A from the apparatus I. Alternatively, the system S comprises an emergency release feature, whereby the bed 20 may be manually moved from the from the scanning volume $V_s$ of the imaging apparatus I, e.g., without a formal procedure. By example only, the emergency release feature comprises a handle H (FIG. 5A) disposed at a foot portion 22 of the bed 20, the emergency release feature configured to override the safety feature and to disengage at least one latch, such as the latching mechanism 350, e.g., in an emergency situation.

Referring to FIG. 2A and FIG. 2B, this diagram illustrates in a perspective view, a smart system S for coupling a medical transporter apparatus A with an imaging apparatus I, in accordance with an embodiment of the present disclosure. The smart system S generally comprises: a smart docking module D, the smart docking module D comprising at least one coupler, such as the active docking module 310, responsive to a controller (not shown) that is operable by a set of executable instructions, the smart docking module D comprising a non-magnetic material, and the smart docking module configured by the controller to automatically perform at least one of: position, dock, engage, latch, lock, interlock, release, emergency-release, quick-release, disengage, emergency-disengage, and quick-disengage the medical transporter apparatus A in relation to the imaging apparatus I. By example only, in this embodiment, the apparatus further comprises guardrails 44 coupled with the table T, wherein the guardrails 44 enhance patient safety as well as facilitate manual movement of the apparatus A, if necessary.

Figure 2C:
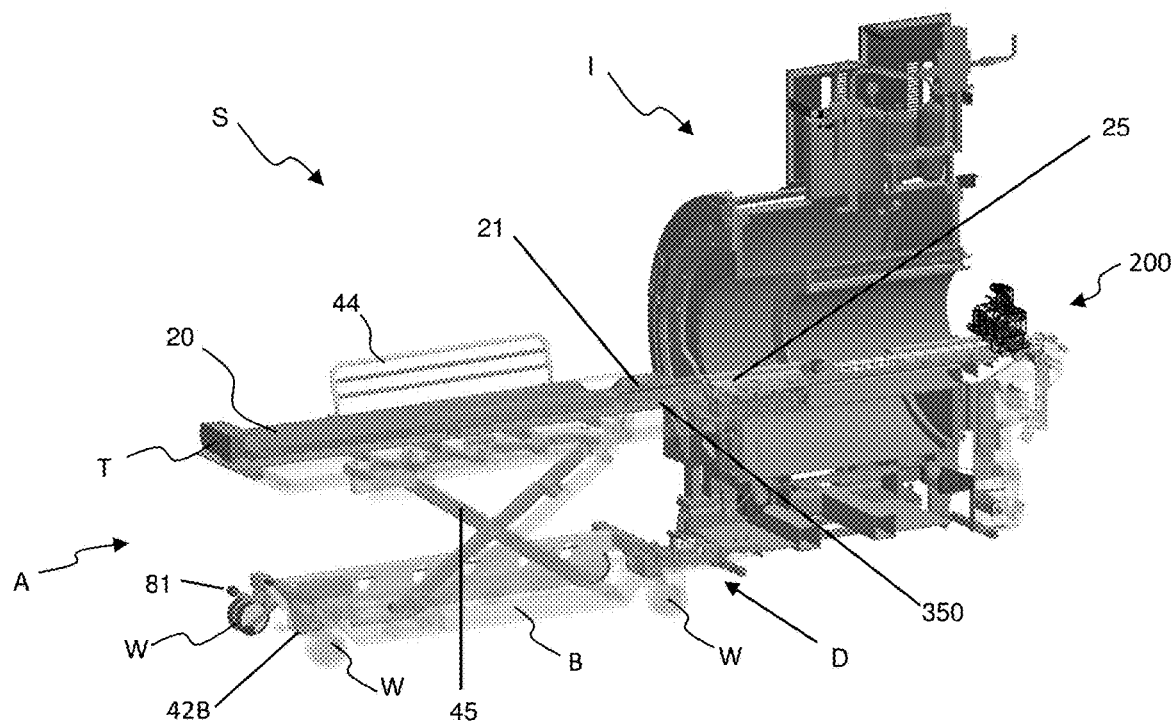
FIG. 2C is a diagram illustrating a cross-sectional perspective view of the smart system for coupling the medical transporter apparatus with the imaging apparatus, as shown in FIGS. 2A and 2B, in accordance with an embodiment of the present disclosure.

Referring to FIG. 2C, this diagram illustrates, in a cross-sectional perspective view, a smart system S for coupling a medical transporter apparatus A with an imaging apparatus I, as shown in FIG. 2A, in accordance with an embodiment of the present disclosure. The at least one wheel W comprises at least one caster wheel, by example only. Each at least one-wheel W, e.g., the rear wheels W, further comprises a wheel locking system, the wheel locking system comprising a wheel lock feature 42a and a wheel unlock feature 42b. The medical transporter apparatus A comprises an elevation or height adjustment feature (not shown) operably coupled with the lift mechanism 45 and a calibration feature (not shown) for calibrating orientation of the bed 20, e.g., in relation to at least one of roll, pitch, and yaw. The height adjustment feature is capable of finely adjusting height within a range of approximately 500 mm to approximately 800 mm, wherein the height is calibrated within +/−5 mm at a height adjustment of approximately 800 mm. The smart docking module D effects coupling the medical transporter apparatus A with the imaging apparatus I; and the smart docking module D is also operable via at least one foot pedal 81 having an associated linkage (not shown).

Still referring to FIG. 2B and FIG. 2C, the smart system S comprises a latching mechanism 350 (FIG. 7), wherein the latching mechanism 350 is coupled with the bed 20 and comprises at least one bed latch 351 for facilitating coupling of the bed 20 with a patient positioner 25 of the apparatus I (FIG. 3A). The patient positioner 25 positions the bed 20, e.g., having the patient P disposed thereon, in the imaging apparatus I. The tongue portion 21 is coupled with the bed 20 and generally comprises an elevation that is higher than that of the bed 20 and is configured for patient ergonomics and well as for seamless engagement with the head coil (not shown). The tongue portion 21 is either integrally or separately formed with the bed 20. The patient positioner 25 provides mechanical control of electrical connections between the head coil and the imaging apparatus I, wherein the head coil optionally translates from the patient positioner 25 toward the tongue portion 21 of the bed 20 to facilitate imaging or scanning. The head coil may be engaged with the tongue portion 21 without undocking, in accordance with some embodiments. Alternatively, the head coil may be stored in relation to the imaging apparatus I, whereby imaging or scanning may be more rapidly performed than in the related art. In another alternative embodiment, the bed 20 holds the head coil.

Referring to FIG. 3A, this diagram illustrates, in a cross-sectional side view, the imaging apparatus I, as shown in FIGS. 2A and 2B, with which the smart system S is implementable, in accordance with embodiments of the present disclosure. The imaging apparatus I comprises a motion system 200, wherein the motion system 200 comprises the patient positioner 25, a belt drive system 26 for actuating the patient positioner 25, and a cable carrier 27 for facilitating at least one of electronic communication and mechanical communication with the patient positioner 25 and for providing cabling to a power source for the patient positioner 25 in moving the bed 20, having the patient P disposed thereon, into, and out of, the scanning volume $V_s$ and for elevationally positioning the bed 20, e.g., in a z-direction. The imaging apparatus I further comprises an emergency disconnect (ED) feature (not shown), the ED feature comprises a mechanical coupling between the patient positioner 25 and the head coil, whereby the head coil is detachable from the patient positioner 25 by applying a force at least that of a predetermined threshold force.

Figure 3B:
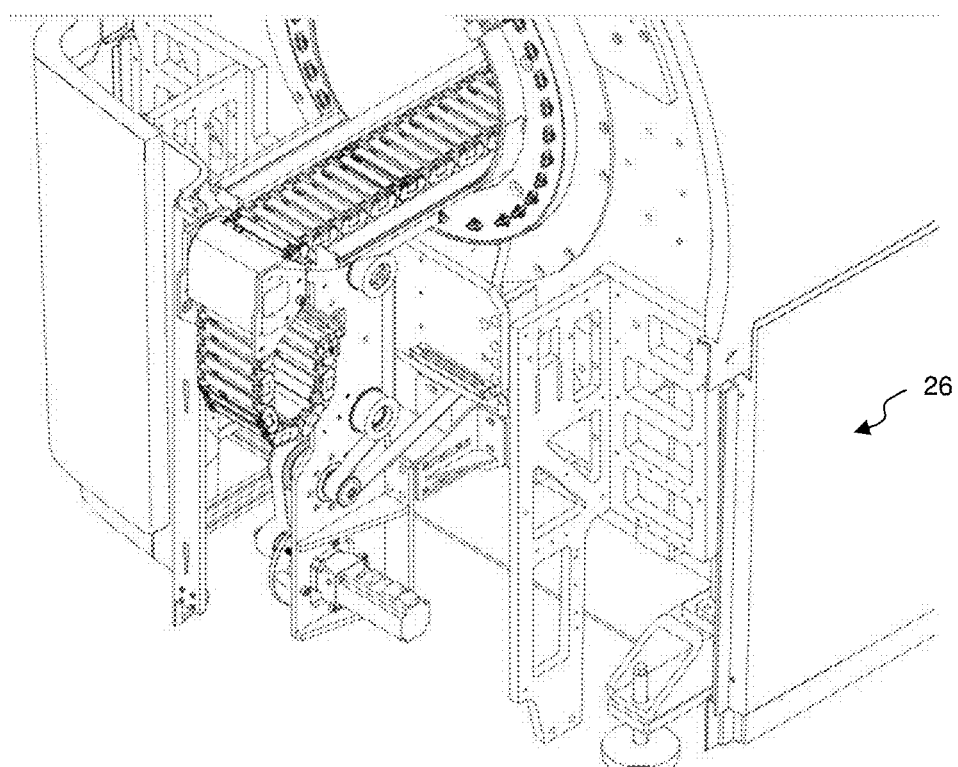
FIG. 3B is a diagram illustrating a perspective view of the belt drive system for actuating the patient positioner, as shown in FIG. 3A, with which the smart system is implementable, in accordance with embodiments of the present disclosure.

Referring to FIG. 3B, this diagram illustrates, in a perspective view, the belt drive system 26, as shown in FIG. 3A, for actuating the patient positioner 25 of the motion system 200 in the imaging apparatus I, with which the smart system S is implementable, in accordance with embodiments of the present disclosure.

Figure 4A:
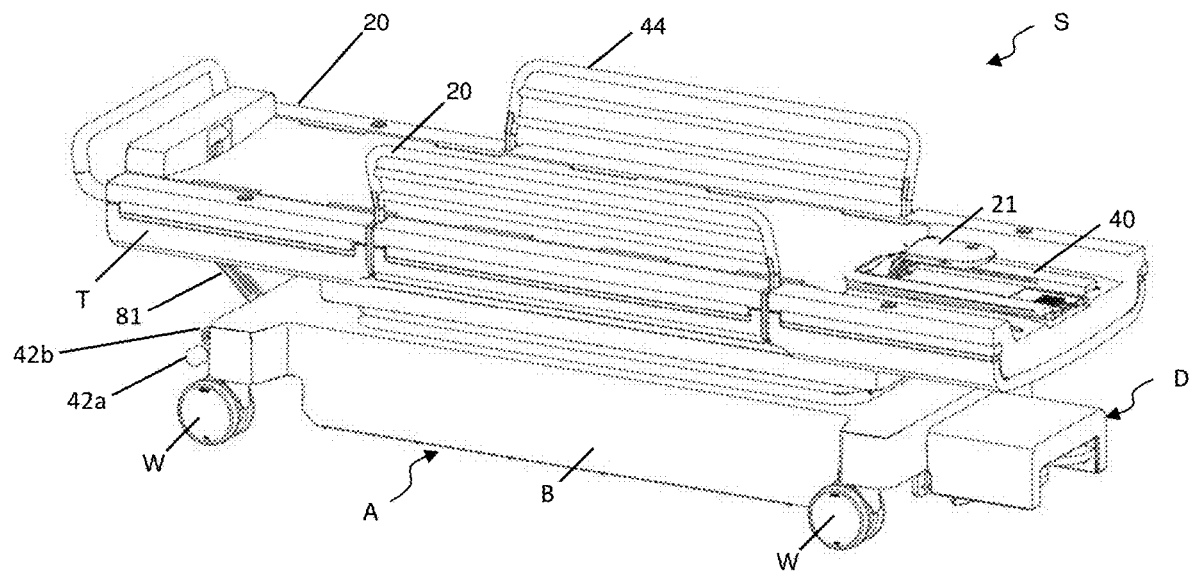
FIG. 4A is a diagram illustrating a perspective view of a smart system, comprising a medical transporter apparatus and a smart docking module, wherein the bed is disposed in a lowest elevational position, in accordance with an embodiment of the present disclosure.

Referring to FIG. 4A, this diagram illustrates, in a perspective view, a smart system S, comprising a medical transporter apparatus A and a smart docking module D, wherein the bed 20 is disposed in a lowest elevational position, in accordance with an embodiment of the present disclosure. The lowest elevational position facilitates disposing the patient P on the bed 20 and for safely transporting the patient P to the imaging apparatus I, e.g., at a lowest center of gravity of the medical transporter apparatus A. The smart docking module D may provide instructions, e.g., from the controller or mechanical communication, to the lifting mechanism 45 regarding a desired elevation, e.g., via a cam-and-cable system.

Figure 4B:
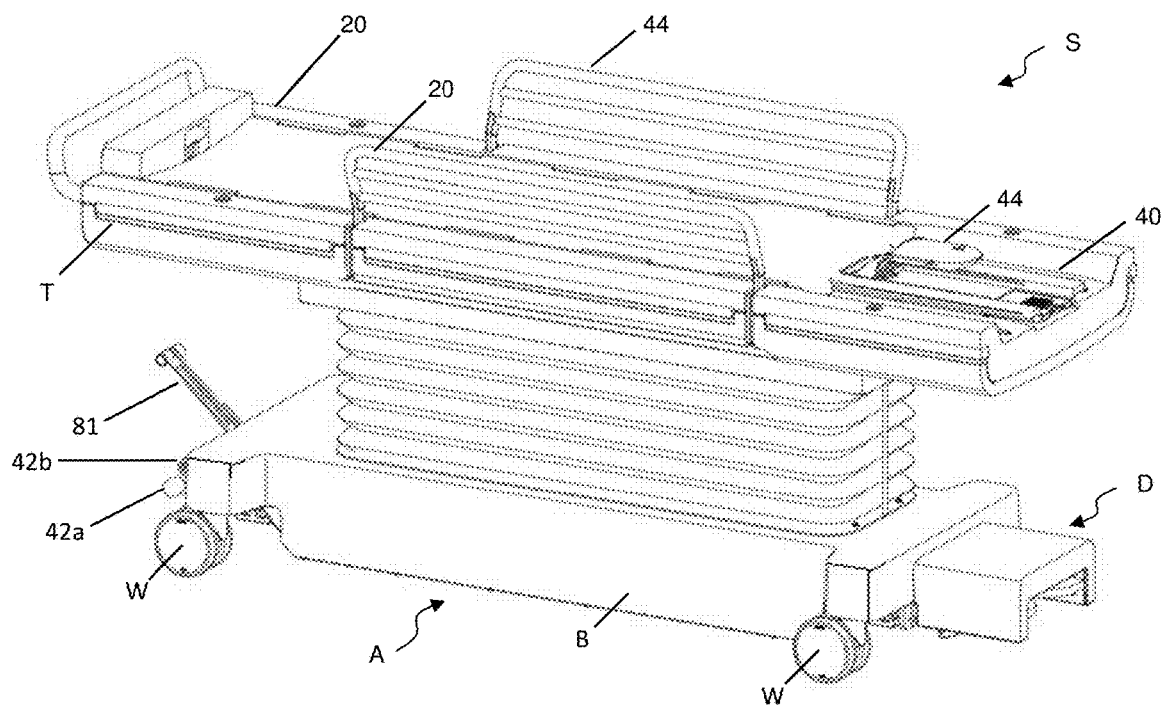
FIG. 4B is a diagram illustrating a perspective view of the smart system, as shown in FIG. 4A, comprising the medical transporter apparatus and the smart docking module, wherein the bed is disposed in a highest elevational position, in accordance with an embodiment of the present disclosure

Referring to FIG. 4B, this diagram illustrates, in a perspective view, the smart system S, as shown in FIG. 4A, comprising the medical transporter apparatus A and the smart docking module D, wherein the bed 20 is disposed in a highest elevational position, in accordance with an embodiment of the present disclosure. The highest elevational position facilitates elevationally positioning the bed 20, e.g., in a z-direction for alignment with the imaging apparatus I. The lifting mechanism 45 comprises a scissor configuration shown without the housing 43, by example only. The lifting mechanism 45 provides a range of elevation motion to facilitate alignment with a Synaptive® MRI machine of any other type of medical equipment.

Referring to FIG. 5, this diagram illustrates, in a perspective view, a smart system S, comprising a medical transporter apparatus A and a smart docking module D, disposed in a highest elevational position, in accordance with an embodiment of the present disclosure. The smart docking module D comprises an active docking module 310 and a passive docking module 320. The passive docking module 320 is configured to couple with the imaging apparatus I, e.g., via a receiver portion R of the imaging apparatus I. The passive docking module 320 comprises a plurality of pins 322. The active docking module comprises a plate portion 311 having a slot 312 for engaging the plurality of pins 322.

Referring to FIG. 5, this diagram illustrates, in a perspective view, a receiver portion R of the imaging apparatus I, with which the smart system S, comprising the medical transporter apparatus A and the smart docking module D, is implementable, in accordance with an embodiment of the present disclosure. The passive docking module 320 is configured to interface, and couple with, the receiver portion R of the imaging apparatus I.

Figure 6A:
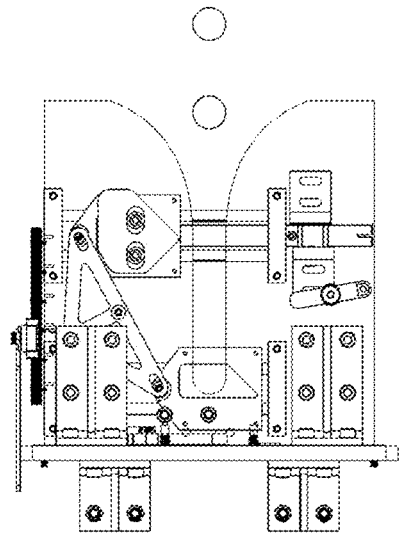
FIG. 6A is a diagram illustrating a top view of the active docking module, as shown in FIG. 5, wherein the active docking module is about to engage (about to dock with) the passive docking module, e.g., when the medical transporter apparatus has been moved proximate the imaging apparatus, in accordance with an embodiment of the present disclosure.

Referring to FIG. 6A, this diagram illustrates, in a top view, a stage at which the active docking module 310, as shown in FIG. 5A, wherein the active docking module is about to engage (about to dock with) the passive docking module 320, e.g., when the medical transporter apparatus A has been moved proximate the imaging apparatus I, in accordance with an embodiment of the present disclosure. The slot 312 of the active docking module 310 aligns with the pins 322 of the passive docking module 320. Thus, the slot 312 is ready to receive the pins 322. The active docking module 310 comprises an interlocking feature 90, wherein the interlocking feature 90 comprises a rotatable arm portion 91 and a plurality of stop portions 92 rotatably coupled with rotatable arm portion 91.

Figure 6B:
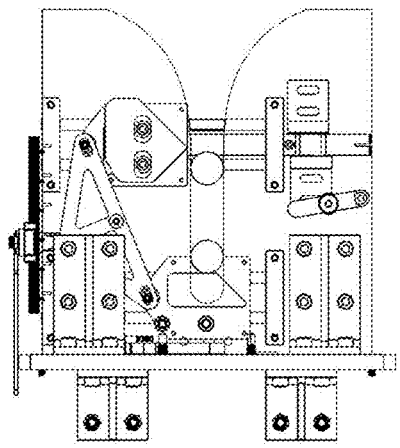
FIG. 6B is a diagram illustrating a top view of the active docking module, as shown in FIG. 5, wherein the active docking module is engaging (docking with) the passive docking module, e.g., when the medical transporter apparatus has been moved closer to the imaging apparatus, in accordance with an embodiment of the present disclosure.

Referring to FIG. 6B, this diagram illustrates, in a top view, a stage at which the active docking module 310, as shown in FIG. 5, wherein the active docking module 310 is engaging (docking with) the passive docking module 320, e.g., when the apparatus A has been moved closer to the imaging apparatus I, in accordance with an embodiment of the present disclosure. The slot 312 of the active docking module 310 accepts the pins 322 of the passive docking module 320. At this stage, the interlocking feature 90 is about to trigger.

Figure 6C:
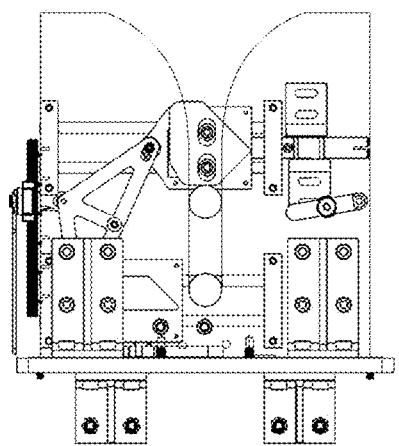
FIG. 6C is a diagram illustrating a top view of the active docking module, as shown in FIG. 5, wherein the active docking module has engaged (docked with) the passive docking module, e.g., when the medical transporter apparatus has been moved as close as possible to the imaging apparatus and when the active docking module is aligned with the passive docking module, in accordance with an embodiment of the present disclosure.

Referring to FIG. 6C, this diagram illustrates, in a top view, a stage at which the active docking module 310, as shown in FIG. 5, wherein the active docking module 310 has engaged (docked with) the passive docking module 320, e.g., when the medical transporter apparatus A has been moved as close as possible to the imaging apparatus I and when the active docking module 310 is aligned with the passive docking module 320, in accordance with an embodiment of the present disclosure. The slot 312 of the active docking module 310 has fully accepted the pins 322 of the passive docking module 320, e.g., a pin 322 is disposed at an end 312e of the slot 312; and the interlocking feature 90 is activated, thereby locking the pins 322 in the slot 312. The pin 322, disposed at the end 312, triggers a stop portion 92, thereby moving the rotatable arm portion 91. Rotation of the arm portion 91 actuates the remaining stop portion 92, thereby locking the pins 322 in the slot 312. The interlocking feature 90 may be spring-loaded and responsive to a predetermined applied force. Rotational direction of the interlocking feature 90 is shown by the arrows 93 for the locking position.

Figure 6D:
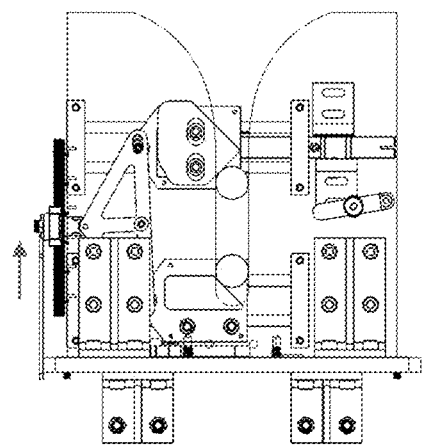
FIG. 6D is a diagram illustrating a top view of the active docking module, as shown in FIG. 5, wherein the active docking module has begun disengaging (begun undocking with) the passive docking module, e.g., when the medical transporter apparatus begins moving away from the imaging apparatus, in accordance with an embodiment of the present disclosure.

Referring to FIG. 6D, this diagram illustrates, in a top view, a stage at which the active docking module 310, as shown in FIG. 5, wherein the active docking module 310 has begun disengaging (begun undocking from) the passive docking module 320, e.g., when the medical transporter apparatus A begins moving away from the imaging apparatus I, in accordance with an embodiment of the present disclosure. The interlocking feature 90 is deactivated, thereby rotating the arm 91 which rotates the stops 92, and thereby unlocking the pins 322 from the slot 312. The slot 312 of the active docking module 310 begins to release the pins 322 of the passive docking module 320, e.g., a pin 322. Rotational direction of the interlocking feature 90 is shown by the arrows 94 for the unlocking position.

Figure 7A:
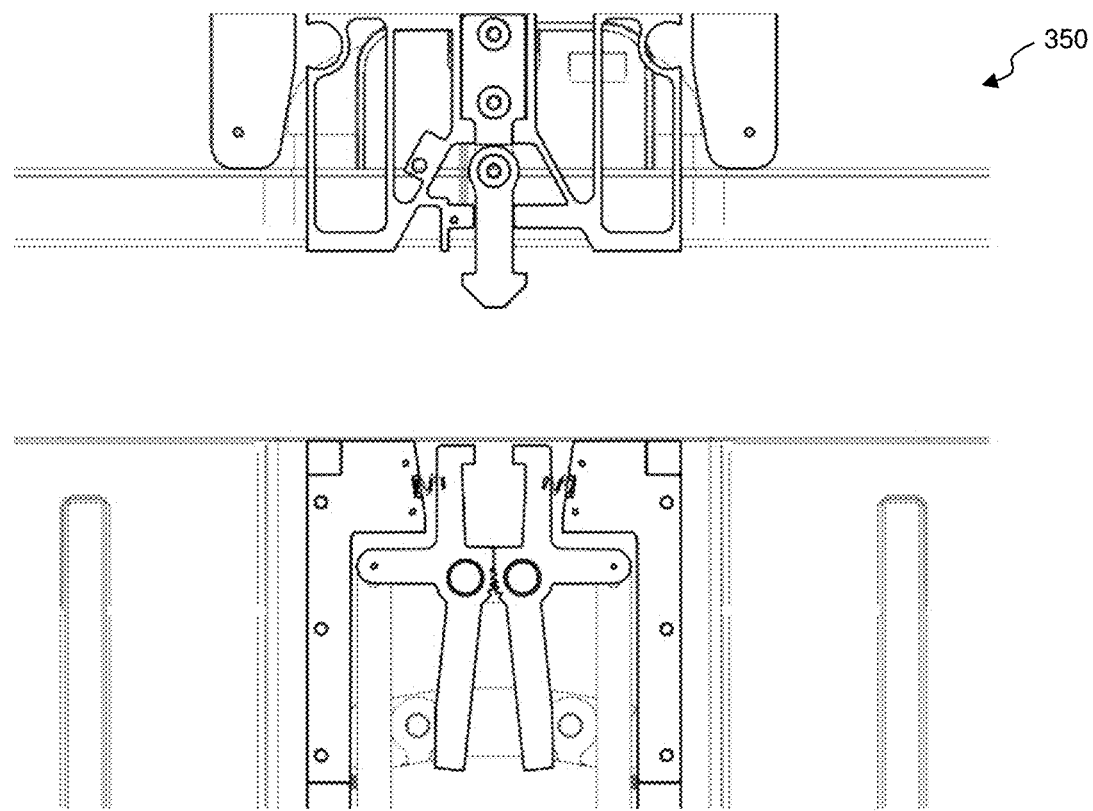
FIG. 7A is a diagram illustrating a top view of a latching mechanism of the smart system, the latching mechanism comprising at least one latch for facilitating coupling of the bed with a patient positioner (PP) of the imaging apparatus, in accordance with an embodiment of the present disclosure.

Referring to FIG. 7A, this diagram illustrates, in a top view, a latching mechanism 350 of the smart system S, the latching mechanism 350 comprising at least one latch, e.g., at least one bed latch 351, for facilitating coupling of the bed 20 with a patient positioner 25 of the apparatus I, in accordance with an embodiment of the present disclosure. The latching mechanism 350 comprises a mechanical structure. The latching mechanism 350 comprises at least one of a non-magnetic material, a stainless steel material, a "316" stainless steel material, an aluminum material, a brass material, a polymeric material, a plastic material, and a composite material. The at least eon bed latch 351 is configured to engage a coupler of the patient positioner 25, such as a coupler 352.

Still referring to FIG. 7A, the latching mechanism 350 is configured to perform at least one of: close for latching the medical transporter T with the medical equipment, e.g., the imaging apparatus I, open for undocking the medical transporter apparatus A from the medical equipment, emergency release the medical transporter apparatus A from the medical equipment. In addition, the latching mechanism 350 comprises a plurality of latches driven by at least one latching cable 330 (FIGS. 15I-15L), wherein the plurality of bed latches 351 is disposable in relation to the bed 20, e.g., via an upper surface of the bed 20, of the medical transporter apparatus A. The latching mechanism 350 further facilitates adjusting the bed 20 to a desired elevation in relation to the medical equipment for accurate docking thereto, wherein the bed 20 is prevented from undesirable movement until the medical transporter apparatus A is docked at the desired elevation. After docking, the latching mechanism 350 is not further actuated unless in response to a further executable instruction to do so or to a manual override in an emergency situation.

Figure 7B:
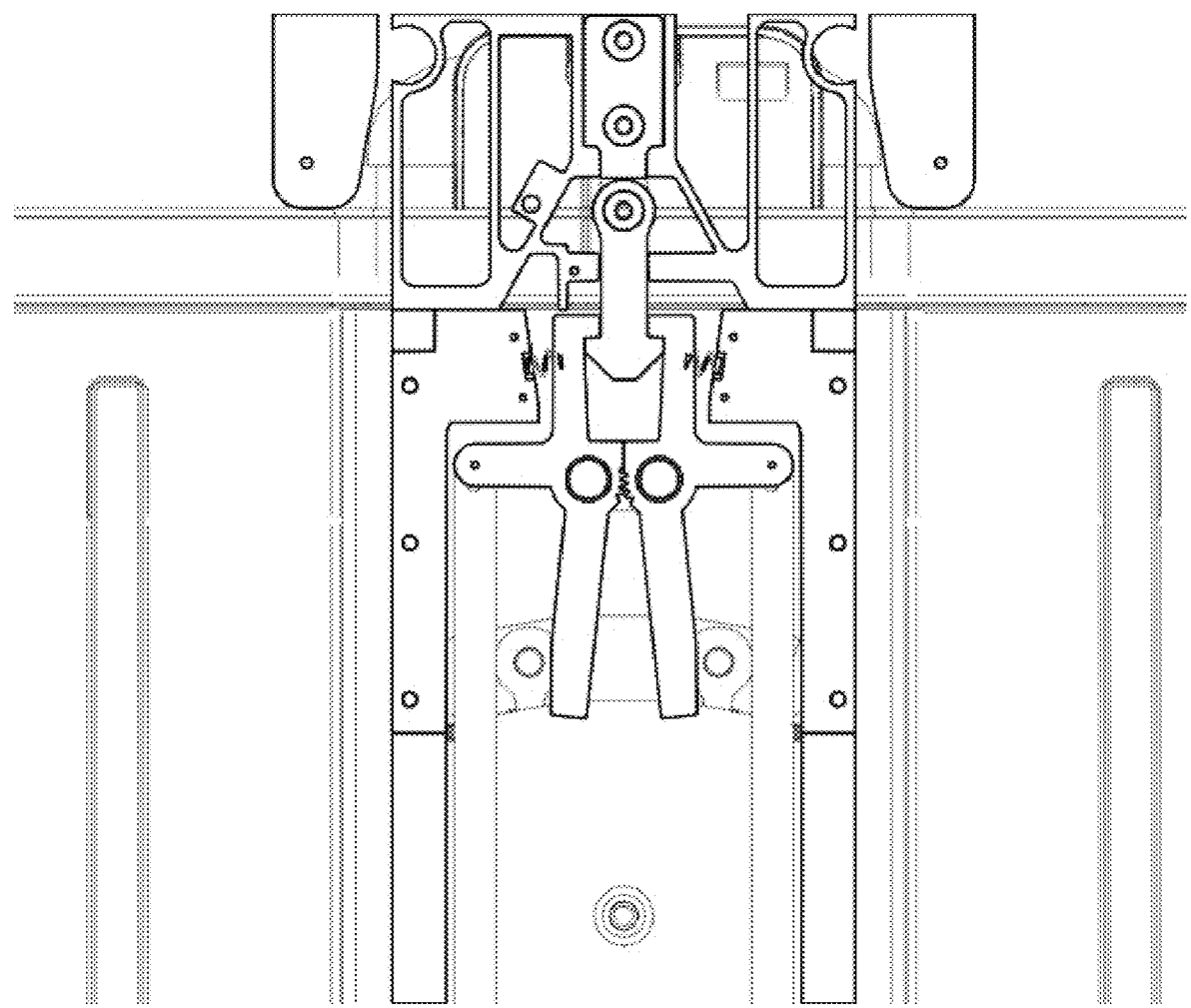
FIG. 7B is a diagram illustrating a view of the latching mechanism, as shown in FIG. 7A, of the smart system, the latching mechanism engaged and latched with the patient positioner of the imaging apparatus, in accordance with an embodiment of the present disclosure.

Referring to FIG. 7B, this diagram illustrates, in a view, the latching mechanism 350, as shown in FIG. 7A, of the smart system S, the latching mechanism 350 engaged and latched with the patient positioner 25 of the apparatus I, in accordance with an embodiment of the present disclosure.

Figure 8B:
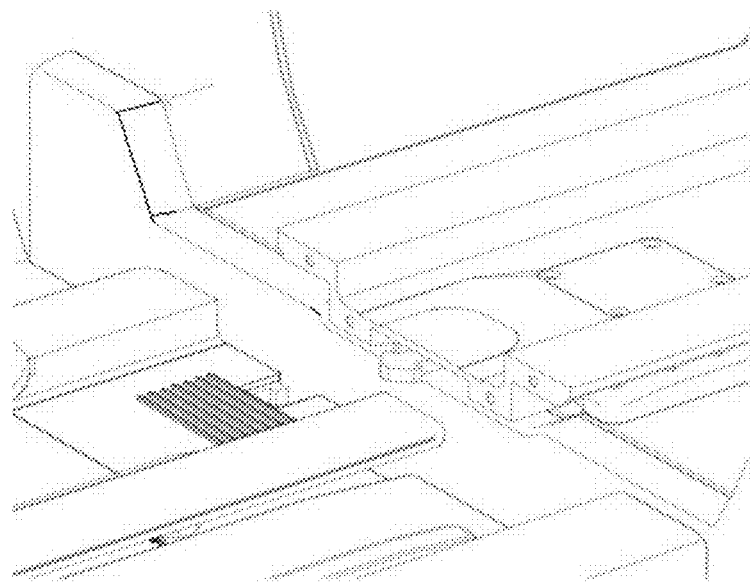
FIG. 8B is a diagram illustrating a partial view of a patient positioner of the imaging apparatus, wherein the patient positioner is preparing to engage a bed, in accordance with an embodiment of the present disclosure.
Figure 8C:
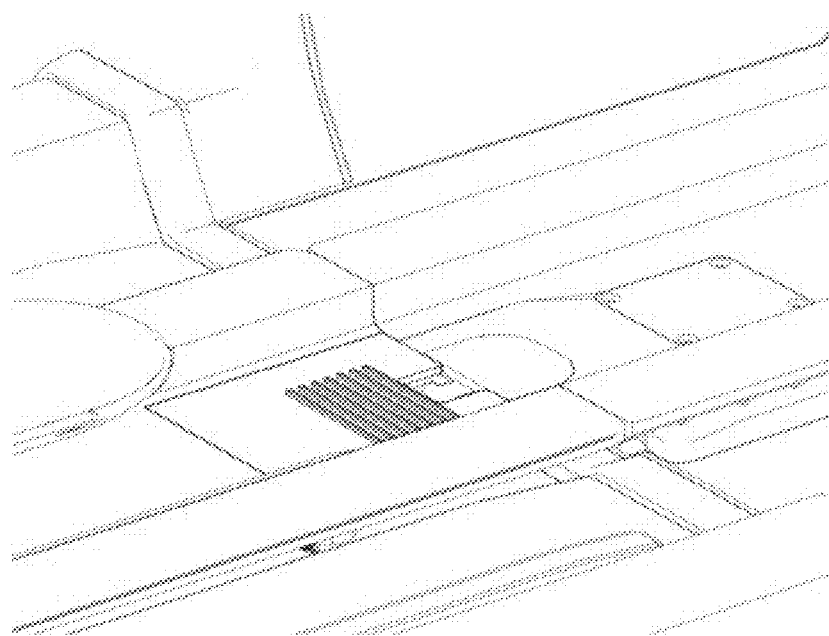
FIG. 8C is a diagram illustrating a perspective view of the smart system, as shown in FIG. 8A, comprising the medical transporter apparatus and the smart docking module, wherein the patient positioner is ready to engage the motor- and rail system for engaging the bed, and wherein the medical transporter apparatus has been docked, at a requisite scanning or imaging height, with the imaging apparatus, in accordance with an embodiment of the present disclosure.

Referring to FIG. 8A, this diagram illustrates, in a perspective view, a smart system S comprising a medical transporter apparatus A and a smart docking module D, wherein the medical transporter apparatus A is docked with an imaging apparatus I, wherein the medical transporter apparatus A is disposed at any height, and wherein the bed 20 is disposed in a "transport" position, and, in a partial view (FIG. 8B), a patient positioner 25 of the imaging apparatus I, wherein the imaging apparatus A is preparing to accommodate the patient P on the bed 20, in accordance with an embodiment of the present disclosure. The smart docking module D comprises the active docking module 310 and the passive docking module 320 which are coupled together at this stage. However, the bed 20 and the table T of the medical transporter apparatus A may be disposed at any elevation at this stage and is adjusted to a requisite height for the engagement with the patient positioner 25 with the motor-and-rail system 40. Referring to FIG. 8B, the patient positioner 25 is shown in its original or "HOME" position, e.g., the patient positioner 25 is still disposed within the scanning volume $V_s$ and does not yet protrude from the scanning volume $V_s$.

Referring to FIG. 8A, this diagram illustrates, in a perspective view, the smart system S, as shown in FIG. 8A, comprising the medical transporter apparatus A and the smart docking module D, e.g., being ready to scan or image, wherein the patient positioner 25 is ready to meet the motor-and rail system 40, e.g., in a flush position, for engaging the bed 20, and wherein the medical transporter apparatus A has been docked, at a requisite scanning or imaging height, with the imaging apparatus I, and, in a partial view, the patient positioner 25 of the imaging apparatus I, wherein the imaging apparatus I is ready to accommodate the bed 20, in accordance with an embodiment of the present disclosure. The active docking module 310 and the passive docking module 320 have been coupled together. At this stage, the bed 20 has now been adjusted to a requisite height for the engagement of the patient positioner 25 and is translatable via the motor-and-rail system 40. Referring to FIG. 8B, the patient positioner 25 is shown in a deployed position, as indicated by the arrow 25a, e.g., a major portion of the patient positioner 25 is disposed within the scanning volume $V_s$ and a minor portion of the patient positioner 25 advances and protrudes from the scanning volume $V_s$, whereby the latching mechanism 350 engages and latches the patient positioner 25. The latching mechanism 350 of the smart system S is disposed at a head portion of the medical transporter apparatus A, such as under the motor-and-rail system 40 and above the table T. The latching mechanism 350 comprises at least one bed latch 351 for facilitating coupling of the bed 20 with the patient positioner 25 of the apparatus I. At this stage, the tongue portion 21 is also engaged with the head coil (not shown).

Figure 9:
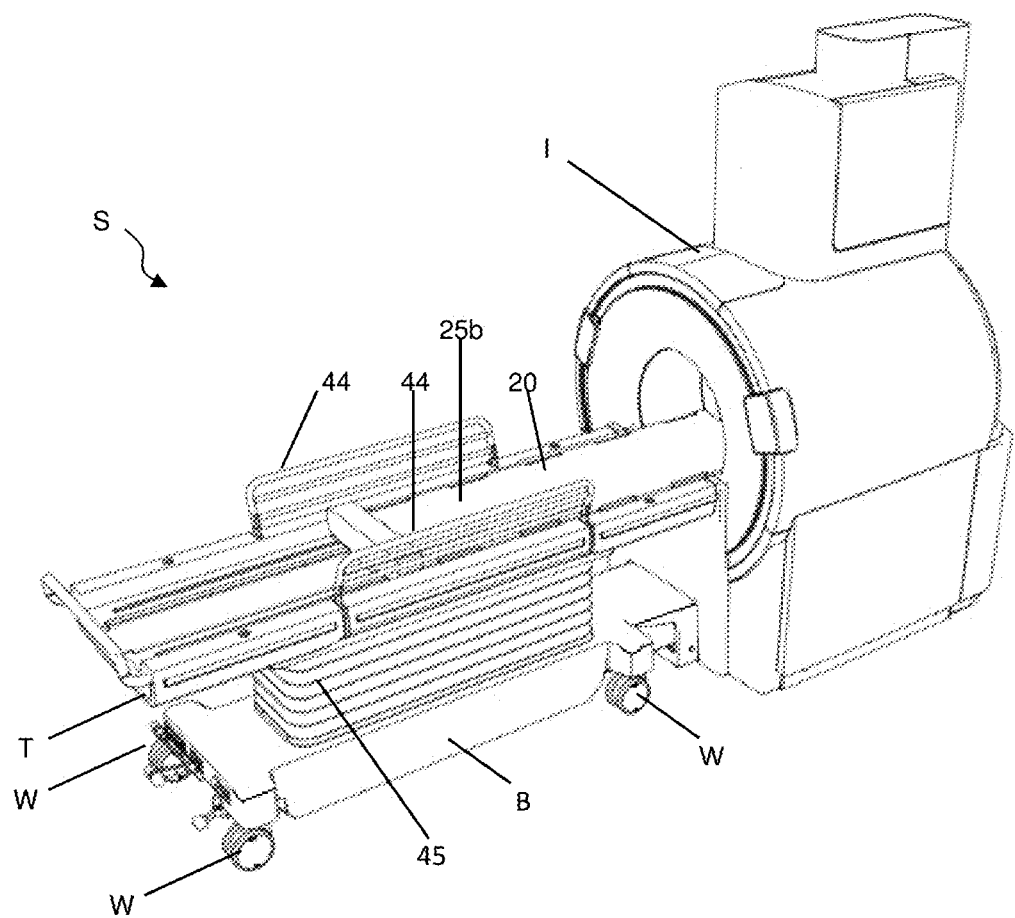
FIG. 9 is a diagram illustrating a perspective view of the smart system, as shown in FIGS. 8A to 8C, comprising the medical transporter apparatus and the smart docking module, wherein the medical transporter apparatus is docked with the imaging apparatus, wherein the bed is in a "scanning" position, wherein the motor-and-rail system is engaged with the patient positioner of the imaging apparatus for translating the bed, wherein the latching mechanism is engaged and latched with the patient positioner, and wherein the bed is pulled into the scanning volume by the patient positioner, in accordance with an embodiment of the present disclosure.

Referring to FIG. 9, this diagram illustrates, in a perspective view, a smart system S, as shown in FIGS. 8A and 8B, comprising the medical transporter apparatus A and the smart docking module D, wherein the transporter apparatus A is docked with an imaging apparatus I, wherein the bed 20 is disposed in a "scanning" position, wherein the motor-and-rail system 40 is flush with the patient positioner 25 for engaging the bed 20 with the patient positioner 25 of the imaging apparatus I. At this stage, for translating the bed 20, wherein the latching mechanism 350 is engaged and latched with the patient positioner 25, wherein the bed 20 is pulled into the scanning volume $V_s$ by the patient positioner 25, e.g., via activating the motion system 200. At this stage, the patient positioner 25 is actuated and draws the bed 20 into the scanning volume $V_s$, in a direction as indicated by arrow 25b, wherein the imaging apparatus A is ready for imaging or scanning the patient P, in accordance with an embodiment of the present disclosure.

Still referring to FIG. 9, for safety, the smart system S requires various interlocks in relation to the medical transporter apparatus A, wherein the bed 20 is constrained and cannot move from the requisite scanning height unless the bed 20 is determined, e.g., by the controller, to be disposed in the "transport" position, wherein the medical transporter apparatus A is constrained from undocking unless the bed 20 is determined to be disposed in the "transport" position, subject to a secondary undocking operation implementable at any time, wherein the bed 20 is constrained and cannot move from the "transport" position unless the medical transporter apparatus A is determined to be fully docked and the bed 20 is determined to be disposed at the requisite scanning height, and wherein the latching mechanism 350 must disengage during at least one of an undocking stage and an emergency extraction of the bed 20 from the scanning volume $V_s$. The smart system S also requires various interlocks in relation to the patient positioner 25 and the motion system 200 of the imaging apparatus I, wherein the patient positioner 25 is prevented from deploying or protruding from the scanning volume $V_s$ for engaging the latching mechanism 350 of the medical transporter apparatus A unless the bed 20 is at determined to be disposed at the requisite scanning height and the medical transporter apparatus A is determined to be fully docked by way of the docking module D. Such determinations are effectable via detectors, e.g., sensors, indicators, e.g., markers or flags, and processor(s) operable by way a set of executable instructions storable in relation to a memory, e.g., a nontransient memory device.

Figure 10A:
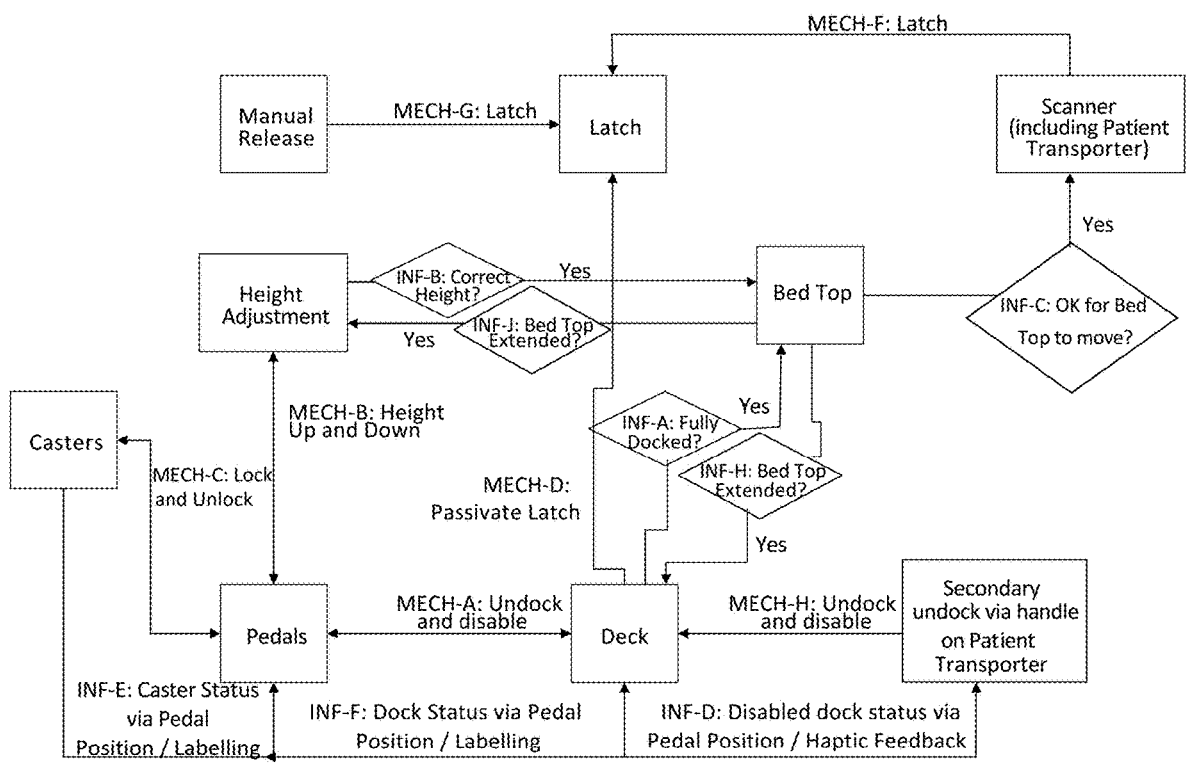
FIG. 10A is a flow diagram illustrating a method of interfacing a medical transporter apparatus with an imaging apparatus, by way of a smart system, using a plurality of interlocks, in accordance with embodiments of the present disclosure.

Referring to FIGS. 10A and 10B, together, this flow diagram and this table, respectively, illustrate and describe a method M of interfacing a medical transporter apparatus A with a piece of medical equipment, e.g., an imaging apparatus I, by way of a smart system S, using a plurality of interlocks, as described in relation to FIG. 9, in accordance with an embodiment of the present disclosure. The plurality of interlock modes comprises five interlock modes, by example only. In an embodiment, the five interlock modes comprises: (1) a bed-undocking interlock mode allows the medical transporter apparatus A to undock from the imaging apparatus I only if the bed 20 is in a "transport" position; (2) a bed-lowering interlock mode allows the medical transporter apparatus A to lower in elevation from a scanning height only if the bed 20 is in a "transport" position; (3) a bed-docking interlock mode allows the bed 20 to move from a "transport" position only if the medical transporter apparatus A is docked with the imaging apparatus I; (4) a bed-elevating interlock mode allows the bed 20 to move from a "transport" position only if the medical transporter apparatus A is at a scanning height; and (5) a latching interlock mode, e.g., via the latching mechanism 350, allows unlatching the bed 20 from the positioner 25 if the medical transporter apparatus A is undocked from the imaging apparatus I. The method M comprises using a set of executable instructions by way of the controller, operable with at least one of software, firmware, and hardware, whereby the controller instructs components, e.g., the interlocking or latching components, of the smart system S. Alternatively, at least one step of the method M may be manually overridden, e.g., in an emergency situation.

Figure 11A:
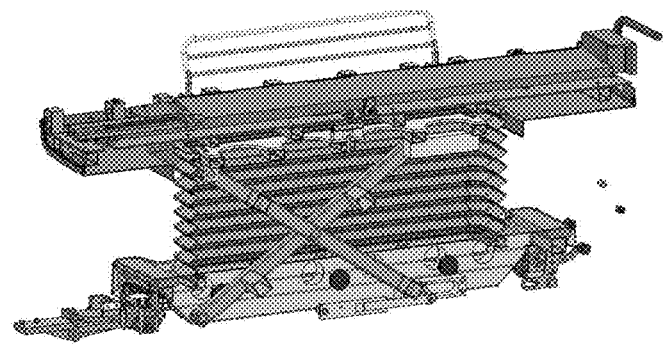
FIGS. 11A and 11B are diagrams illustrating respective perspective views of a smart system, comprising a medical transporter apparatus and a smart docking module, in accordance with an embodiment of the present disclosure.
Figure 11B:
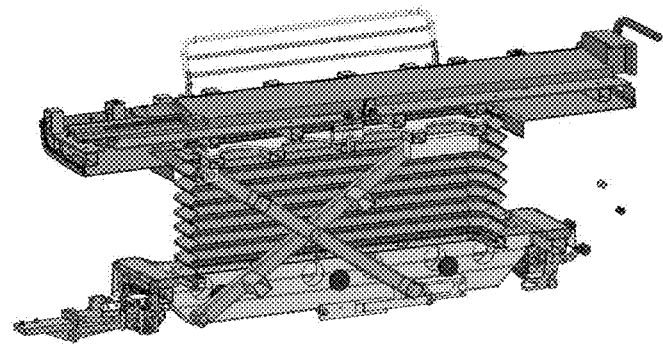

Referring to FIGS. 11A and 11B, these diagrams illustrate, in respective perspective views, a system S, comprising a medical transporter apparatus A and a smart docking module D, and, in respective partial view (FIG. 11C), a bed 20 respectively interlocked and released for adjusting elevation relative to a base B by way of an interlock cam system 360, in accordance with an embodiment of the present disclosure. The interlock cam system 360 comprises a cam 361 and a cam cable 317, wherein retracting the bed 20 in relation to the table T comprises tensioning the cable via rotating the cam 361 in a direction as indicated by arrow 11a, and wherein releasing the bed 20 in relation to the table T comprises releasing tension in the cable via rotating the cam 361 in a direction as indicated by arrow 11b.

Still referring to FIGS. 11A and 11B, the cam 361 is actuable by an interlocking foot pedal system 370 (FIG. 12). The interlocking foot pedal system 370 comprises a first foot pedal 371 for actuating the bed 20 into a neutral position and a second foot pedal 372 for adjusting elevation of the bed 20, wherein the second foot pedal 372 is disabled when the bed 20 is extended toward or into the scanning volume $V_s$. The interlocking foot pedal system 370 comprises a pump (not shown) for adjusting elevation of the bed 20. The pump is configured to actuate the table T, e.g., by way of a "scissor" lift mechanism or any other elevator mechanism. The smart system S further comprises at least one detector, e.g., at least one sensor 110, disposed in relation to the imaging apparatus I, at least one indicator, e.g., a "flag" 120, e.g., disposed in relation to the apparatus A, and at least one photo-interrupter 130 disposed in relation to the imaging apparatus I, e.g., the MRI machine.

Figure 11C:
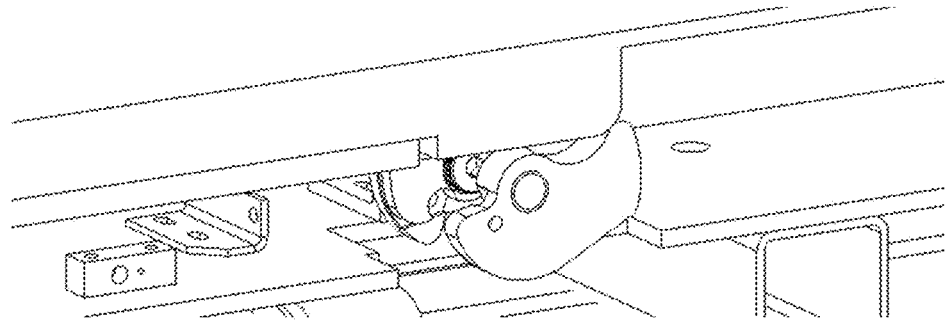
FIGS. 11C and 11D are diagrams illustrating respective partial views of a bed respectively interlocked and released for adjusting elevation relative to a base by way of an interlock cam system, in accordance with an embodiment of the present disclosure.
Figure 11D:
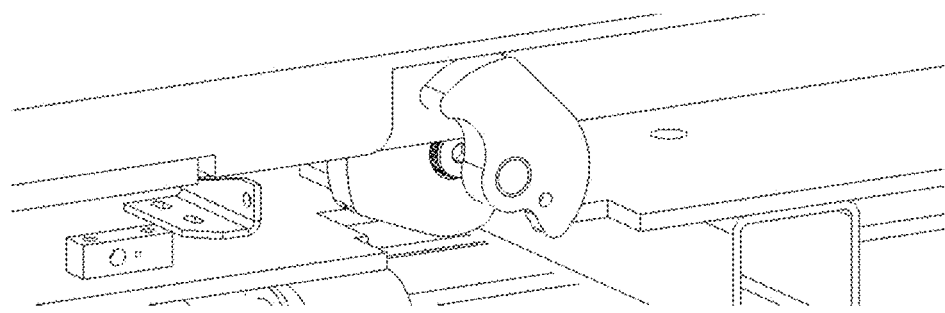
Figure 12A:
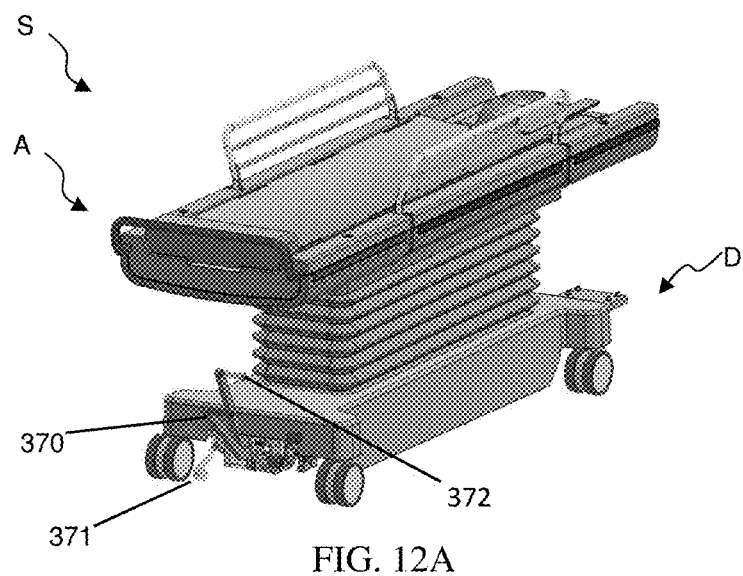
FIGS. 12A and 12B are diagrams illustrating respective perspective views of the smart system, as shown in FIGS. 11A and 11B, comprising the medical transporter apparatus and the smart docking module, in accordance with an embodiment of the present disclosure.
Figure 12B:
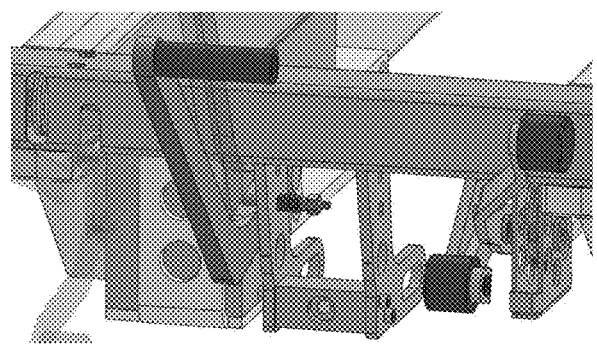
Figure 12C:
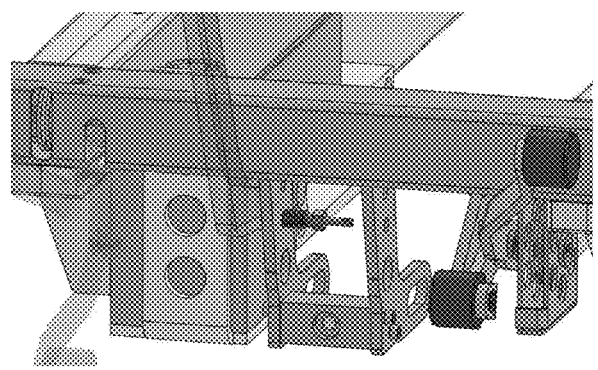

Referring to FIGS. 12A and 12B, these diagrams illustrate, in respective perspective views, the smart system S, as shown in FIGS. 11A and 11D, comprising the medical transporter apparatus A and the smart docking module D, and, in respective partial views (FIGS. 12C and 12D), the bed 20 respectively interlocked and released for adjusting elevation relative to the base B by way of an interlocking foot pedal system 370, in accordance with an embodiment of the present disclosure. The interlocking foot pedal system 370 comprises a first foot pedal 371 for actuating the bed 20 into a neutral position and a second foot pedal 372 for adjusting elevation of the bed 20, wherein the second foot pedal 372 is disabled when the bed 20 is extended toward or into the scanning volume $V_s$. The pedal 372 is operable by raising in order to lower elevation of the bed 20. When the bed 20 is determined to be in an extended position, a plunger 373 is deployed, thereby disabling operation of the pedal 372, thereby interlocking a height adjustment, whereby elevation of the bed 20 is not adjustable. When the bed 20 is determined to be in a "transport" position, the plunger 373 is retracted, thereby enabling operation of the pedal 372, whereby elevation of the bed 20 is adjustable. Determinations may be made by the controller.

Figure 13A:
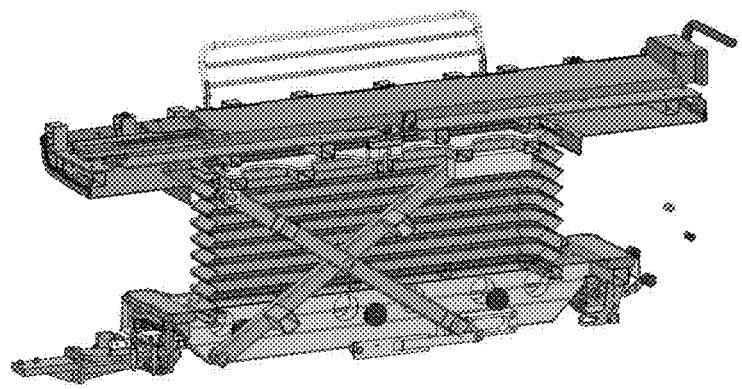
FIGS. 13A and 13B are diagrams illustrating respective perspective views of the smart system, as shown in FIGS. 11A and 11B, comprising the medical transporter apparatus and the smart docking module, in accordance with an embodiment of the present disclosure.
Figure 13B:
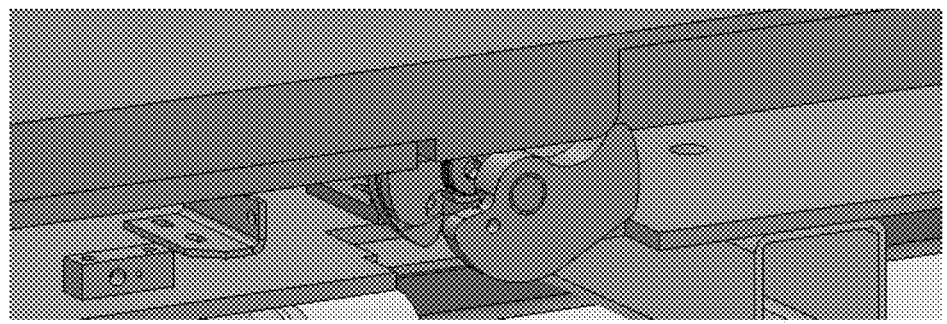
Figure 13C:
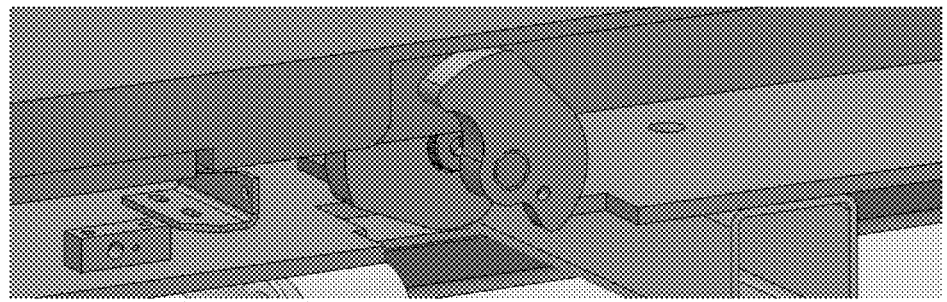
FIG. 13C is a diagram illustrating a respective partial view of the bed respectively interlocked and released for adjusting translation relative to the table by way of an interlock cam system, in accordance with an embodiment of the present disclosure.

Referring to FIGS. 13A and 13B, these diagrams illustrate, in respective perspective views, the smart system S, as shown in FIGS. 11A and 11D, comprising the medical transporter apparatus A and the smart docking module D, and, in respective partial view (FIG. 13C), the bed 20 respectively interlocked and released in relation to the table T by way of an interlock cam system 360, in accordance with an embodiment of the present disclosure. As described herein, the interlock cam system 360 comprises a cam 361 and a cam cable 317, wherein retracting the bed 20 in relation to the table T comprises tensioning the cam cable 317 via rotating the cam 361 in a direction as indicated by arrow 11a, and wherein releasing the bed 20 in relation to the table T comprises releasing tension in the cam cable 317 via rotating the cam 361 in a direction as indicated by arrow 11b. The cam 361 is actuable by an interlocking foot pedal system 370 (FIGS. 12A-12D). The interlocking foot pedal system 370 comprises a first foot pedal 371 for actuating the bed 20 into a neutral position and a second foot pedal 372 for adjusting elevation of the bed 20, wherein the second foot pedal 372 is disabled when the bed 20 is extended toward or into the scanning volume $V_s$. Input from the interlock cam system 360 is required for docking via the docking module D.

Figure 14A:
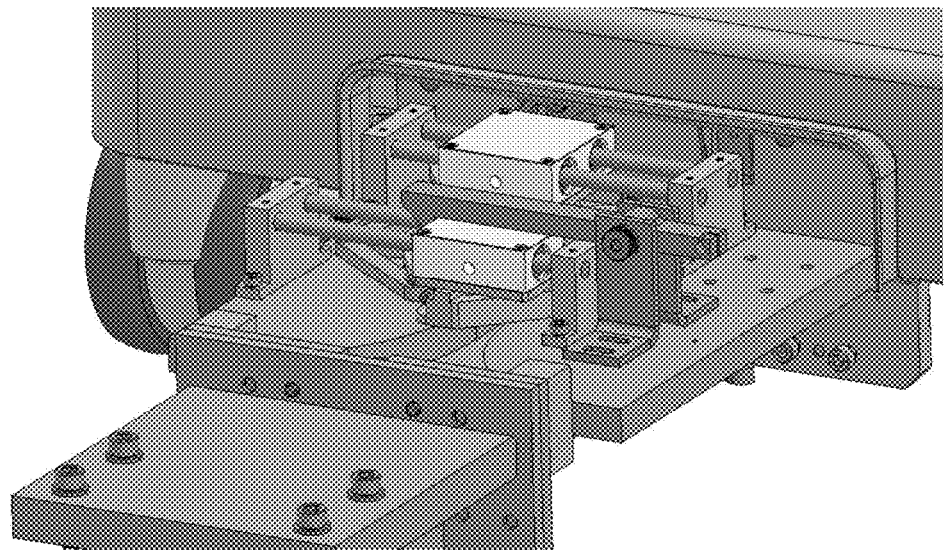
FIG. 14A is a diagram illustrating a perspective view of the smart docking module, comprising the active docking module and the passive docking module, wherein the active docking module, as shown in FIG. 6C, has engaged, docked, and locked with the passive docking module, in accordance with an embodiment of the present disclosure.

Referring to FIG. 14A, this diagram illustrates, in a perspective view, the smart docking module D, comprising the active docking module 310 and the passive docking module 320, wherein the active docking module 310, as shown in FIG. 6C, has engaged, docked, and locked with the passive docking module 320, in accordance with an embodiment of the present disclosure. If the bed 20 is determined to be in an extended position, an active docking latch 315 facilitates retention of the pins 322 in the slot 312 by actuating the interlocking feature 90, whereby undocking of the medical transporter apparatus A from the imaging apparatus I is prevented.

Figure 14B:
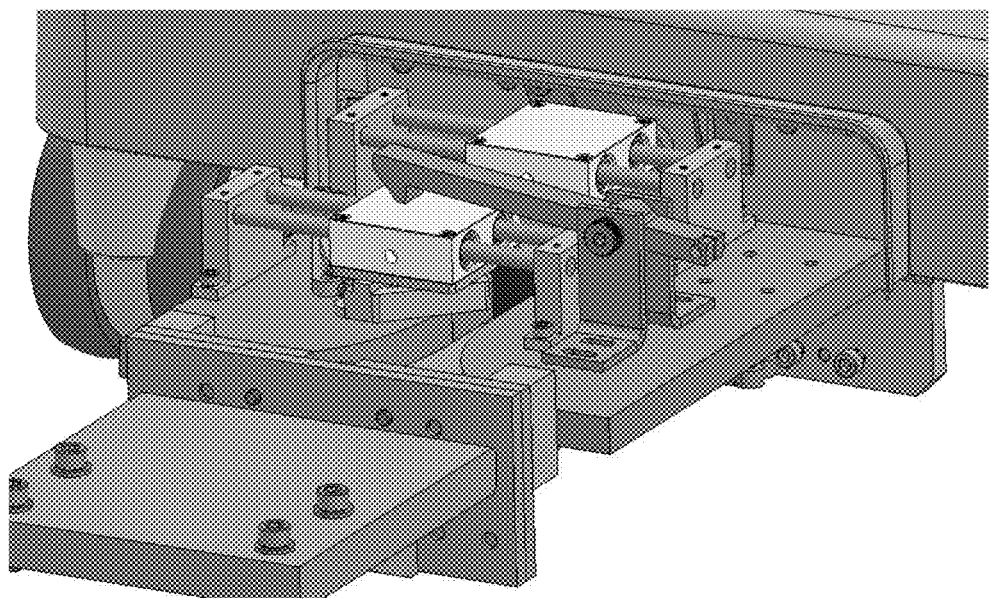
FIG. 14B is a diagram illustrating a perspective view of the active docking module of the smart docking module, wherein the active docking module, as shown in FIG. 6D, is disengaging, undocking, and unlocking with the passive docking module, in accordance with an embodiment of the present disclosure.

Referring to FIG. 14B, this diagram illustrates, in a perspective view, the smart docking module D, comprising the active docking module 310 and the passive docking module 320, wherein the active docking module 310, as shown in FIG. 6D, is disengaging, undocking, and unlocking with the passive docking module 320, in accordance with an embodiment of the present disclosure. If the bed 20 is determined to be in a "transport" position, the active docking latch 315 is actuated by the cam cable 317 (FIG. 15A) tensioned in a direction as indicated by the arrow 316, thereby disengaging the active docking latch 315 from the interlocking feature 90, and thereby releasing the pins 322 from the slot 312, whereby undocking of the apparatus A is enabled.

Figure 14C:
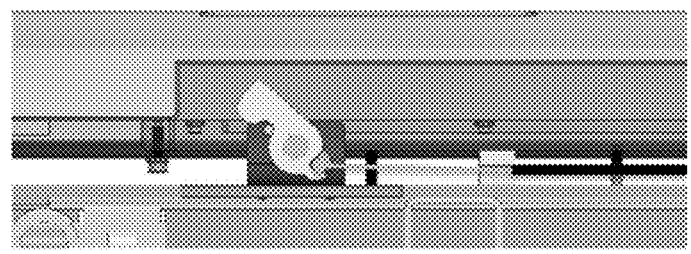
FIG. 14C is diagram illustrating a side view of the interlock cam system, comprising the cam and the cam cable, wherein one end of the cam cable is coupled with the cam, wherein the bed is deployed or extended for interlocking the height thereof, wherein the bed is disposed in the "scanning" position, and whereby the interlock cam system provides input to the active docking module of the smart docking module, in accordance with an embodiment of the present disclosure.

Referring to FIG. 14C, this diagram illustrates, in a side view, the interlock cam system 360, comprising the cam 361 and the cam cable 317, wherein one end 317a of the cam cable 317 is coupled with the cam 361, wherein the bed 20 is deployed or extended for interlocking the height thereof, wherein the bed 20 is disposed in the "scanning" position, whereby the cam 361 rotates in a direction indicated by arrow 11b, whereby tension in the cam cable 317 is released, and whereby the interlock cam system 360 provides input to the active docking module 310 of the smart docking module D, in accordance with an embodiment of the present disclosure.

Figure 14D:
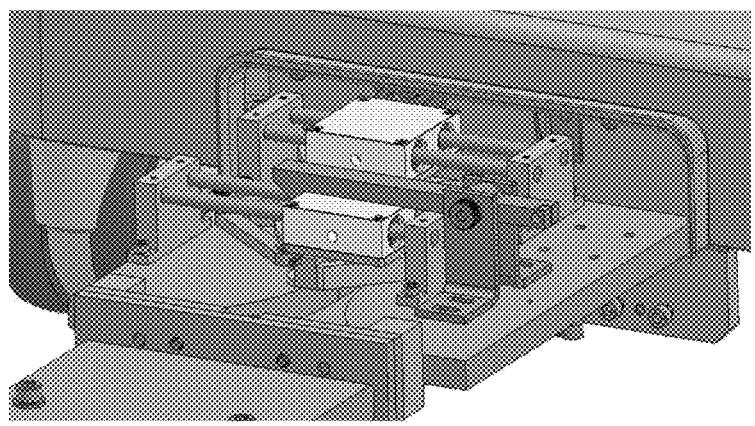
FIG. 14D is a diagram illustrating a perspective view of the smart docking module, comprising the active docking module and the passive docking module, wherein input from the interlock cam system, as shown in FIG. 14C, effectively actuates the active docking latch via an end of an active docking cable, and whereby the medical transporter apparatus is docked and locked in relation to the imaging apparatus, in accordance with an embodiment of the present disclosure.

Referring to FIG. 14D, this diagram illustrates, in a perspective view, the smart docking module D, comprising the active docking module 310 and the passive docking module 320, wherein input from the interlock cam system 360, as shown in FIG. 14C, effectively actuates the active docking latch 315 via an end 318a of an active docking cable 318, the active docking cable 318 operably coupled with the cam cable 317, whereby output is provided by the active docking module 310 in relation to the passive docking module 320, wherein actuation of the active docking latch 315 actuates the interlocking feature 90, wherein actuation of the arm 91 actuates the stops 92, whereby the pins 322 are retained within the slot 312, and whereby the medical transporter apparatus A is docked and locked in relation to the imaging apparatus I, in accordance with an embodiment of the present disclosure.

Figure 14E:
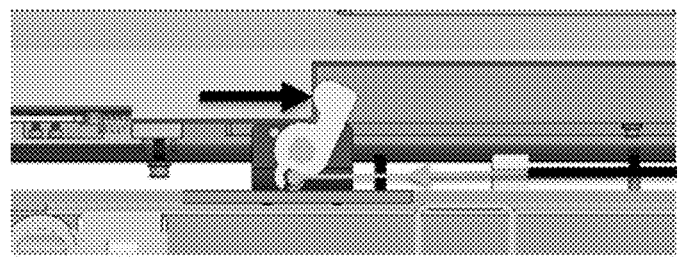
FIG. 14E is a diagram illustrating a side view of the interlock cam system, comprising the cam and the cam cable, one end of the cam cable coupled with the cam, wherein the bed is undeployed or retracted for unlocking the height thereof, wherein the bed is disposed in the "transport" position, and whereby the interlock cam system provides input to the active docking module of the smart docking module, in accordance with an embodiment of the present disclosure.

Referring to FIG. 14E, this diagram illustrates, in a side view, the interlock cam system 360, comprising the cam 361 and the cam cable 317, wherein one end 317a of the cam cable 317 is coupled with the cam 361, wherein the bed 20 is undeployed or retracted for unlocking the height thereof, wherein the bed 20 is disposed in the "transport" position, whereby the cam 361 rotates in a direction indicated by arrow 11a, whereby tension in the cam cable 317 is applied, and whereby the interlock cam system 360 provides input to the active docking module 310 of the smart docking module D, in accordance with an embodiment of the present disclosure.

Figure 14F:
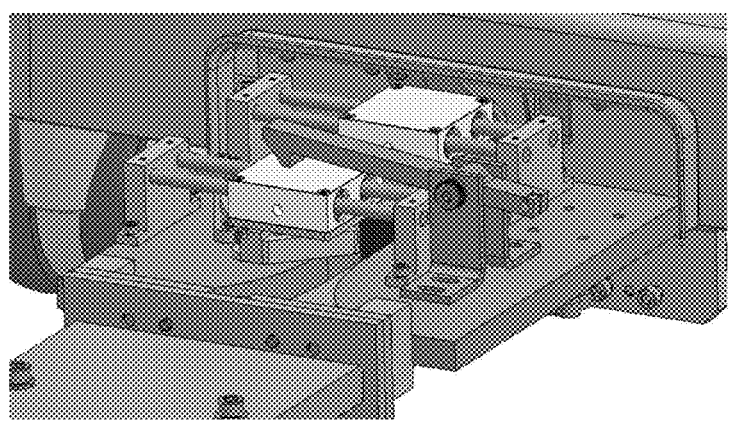
FIG. 14F is a diagram illustrating a perspective view of the smart docking module, comprising the active docking module and the passive docking module, wherein input from the interlock cam system, as shown in FIG. 14E, effectively releases the active docking latch via an end of the active docking cable, and whereby the medical transporter apparatus is unlocked and undocked in relation to the imaging apparatus, in accordance with an embodiment of the present disclosure.

Referring to FIG. 14F, this diagram illustrates, in a perspective view, the smart docking module D, comprising the active docking module 310 and the passive docking module 320, wherein input from the interlock cam system 360, as shown in FIG. 14E, effectively releases the active docking latch 315 via the opposing end 318a of the active docking cable 318, the active docking cable 318 operably coupled with the cam cable 317, whereby output is provided by the active docking module 310 in relation to the passive docking module 320, wherein actuation of the active docking latch 315 retracts the interlocking feature 90, wherein retraction of the arm 91 retracts the stops 92, whereby the pins 322 are released from the slot 312, and whereby the medical transporter apparatus A is unlocked and undocked in relation to the imaging apparatus I, in accordance with an embodiment of the present disclosure.

Figure 14G:
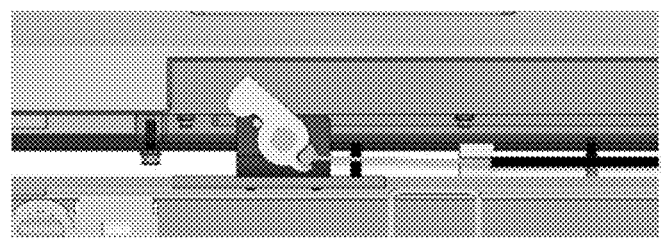
FIG. 14G is a diagram illustrating a side view of the interlock cam system, comprising the cam and the cam cable, wherein one end of the cam cable is coupled with the cam, wherein the bed is deployed or extended for interlocking the height thereof, wherein the bed is disposed in the "scanning" position, and whereby the interlock cam system provides input to the interlocking foot pedal system, in accordance with an embodiment of the present disclosure.

Referring to FIG. 14G, this diagram illustrates, in a side view, the interlock cam system 360, comprising the cam 361 and the cam cable 317, wherein one end 317a of the cam cable 317 is coupled with the cam 361, wherein the bed 20 is deployed or extended for interlocking the height thereof, wherein the bed 20 is disposed in the "scanning" position, whereby the cam 361 rotates in a direction indicated by arrow 11b, whereby tension in the cam cable 317 is released, and whereby the interlock cam system 360 provides input to the interlocking foot pedal system 370, in accordance with an embodiment of the present disclosure.

Figure 14H:
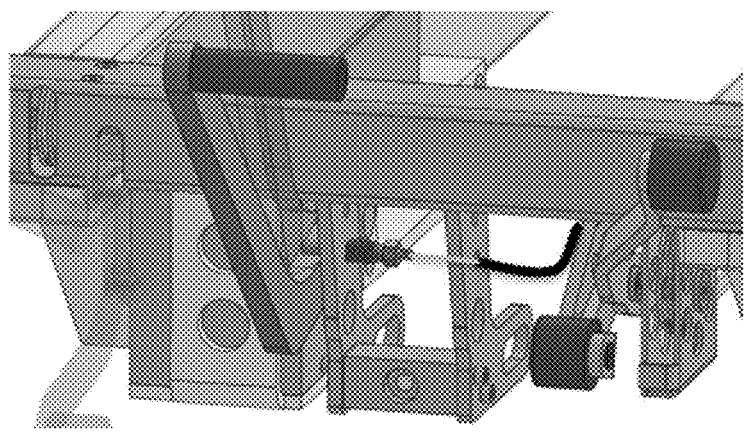
FIG. 14H is a diagram illustrating a perspective view of the interlocking foot pedal system, comprising a first foot pedal for actuating the bed into a neutral position and a second foot pedal for adjusting elevation of the bed, wherein input from the interlock cam system, as shown in FIG. 14G, effectively prevents actuation of the second foot pedal via an end of a foot pedal cable operably coupled with the cam cable, and whereby the medical transporter apparatus is constrained from lowering, in accordance with an embodiment of the present disclosure.

Referring to FIG. 14H, this diagram illustrates, in a perspective view, the interlocking foot pedal system 370, comprising a first foot pedal 371 for actuating the bed 20 into a neutral position and a second foot pedal 372 for adjusting elevation of the bed 20, wherein input from the interlock cam system 360, as shown in FIG. 14G, effectively prevents actuation of the second foot pedal 372 via an end 319a of a foot pedal cable 319, the foot pedal cable 319 operably coupled with the cam cable 317, whereby output is provided to the interlocking foot pedal system 370, wherein actuation of the end 319a of the foot pedal cable 319 actuates a plunger 319b, whereby movement of the second foot pedal 372 is disabled, whereby the second foot pedal 372 is constrained from lifting, and whereby the medical transporter apparatus A is constrained from lowering, in accordance with an embodiment of the present disclosure.

Figure 14I:
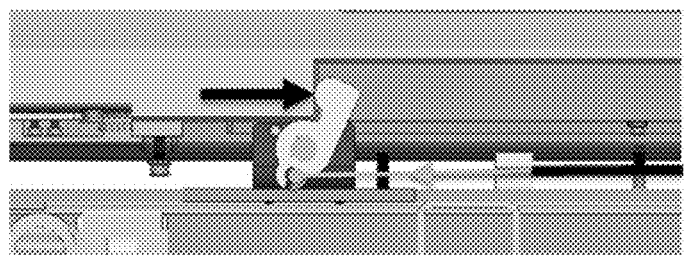
FIG. 14I is a diagram illustrating a side view of the interlock cam system, comprising the cam and the cam cable, wherein one end of the cam cable is coupled with the cam, wherein the bed is undeployed or retracted for unlocking the height thereof, wherein the bed is disposed in the "transport" position, and whereby the interlock cam system provides input to the interlocking foot pedal system, in accordance with an embodiment of the present disclosure.

Referring to FIG. 14I, this diagram illustrates, in a side view, the interlock cam system 360, comprising the cam 361 and the cam cable 317, wherein one end 317a of the cam cable 317 is coupled with the cam 361, wherein the bed 20 is undeployed or retracted for unlocking the height thereof, wherein the bed 20 is disposed in the "transport" position, whereby the cam 361 rotates in a direction indicated by arrow 11b, whereby tension in the cam cable 317 is released, and whereby the interlock cam system 360 provides input to the interlocking foot pedal system 370, in accordance with an embodiment of the present disclosure.

Figure 14J:
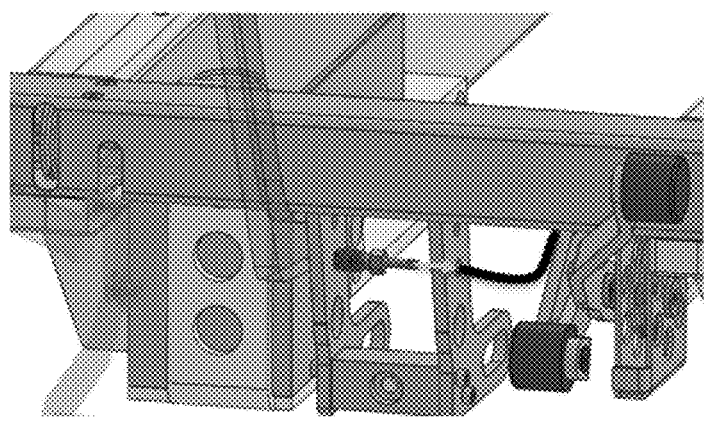
FIG. 14J is a diagram illustrating a perspective view of the interlocking foot pedal system, comprising a first foot pedal for actuating the bed into a neutral position and a second foot pedal for adjusting elevation of the bed, wherein input from the interlock cam system, as shown in FIG. 14I, effectively allows actuation of the second foot pedal via an end of a foot pedal cable operably coupled with the cam cable, and whereby the medical transporter apparatus is enabled for lowering, in accordance with an embodiment of the present disclosure.

Referring to FIG. 14J, this diagram illustrates, in a perspective view, the interlocking foot pedal system 370, comprising a first foot pedal 371 for actuating the bed 20 into a neutral position and a second foot pedal 372 for adjusting elevation of the bed 20, wherein input from the interlock cam system 360, as shown in FIG. 14I, effectively allows actuation of the second foot pedal 372 via an end 319a of a foot pedal cable 319, the foot pedal cable 319 operably coupled with the cam cable 317, whereby output is provided to the interlocking foot pedal system 370, wherein actuation of the end 319a of the foot pedal cable 319 retracts the plunger 319b, whereby movement of the second foot pedal 372 is enabled, whereby the second foot pedal 372 is enabled for lifting, and whereby the medical transporter apparatus A is enabled for lowering, in accordance with an embodiment of the present disclosure.

Figure 15A:
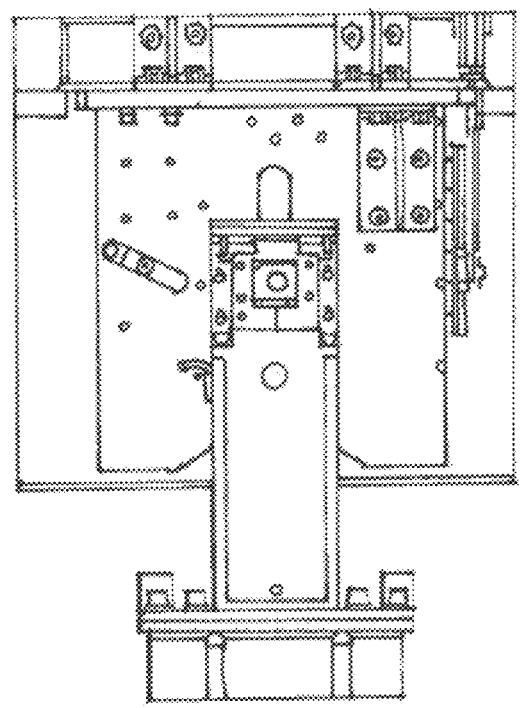
FIG. 15A is a diagram illustrating a bottom view of a smart docking module, comprising an active docking module and a passive docking module, wherein the active docking module, as shown in FIG. 6D, is disengaging, undocking, and unlocking with the passive docking module, in accordance with an embodiment of the present disclosure.

Referring to FIG. 15A, this diagram illustrates, in a bottom view, the smart docking module D, comprising the active docking module 310 and the passive docking module 320, wherein the active docking module 310, as shown in FIG. 6D, is unlocking, disengaging, and undocking in relation to the passive docking module 320, in accordance with an embodiment of the present disclosure. If the bed 20 is determined to be in a "transport" position, an active docking latch 315 is actuated by a cam cable 317 tensioned in a direction as indicated by the arrow 316 (FIG. 14B), thereby disengaging the active docking latch 315 from the arm 91 and stops 92, and thereby releasing the pins 322 from the slot 312, whereby undocking of the medical transporter apparatus A is enabled. The cam cable 317 is operably coupled with the interlock cam system 360 and actuates a dock interlock lever 313 which, in turn, actuates the active docking latch 315.

Figure 15B:
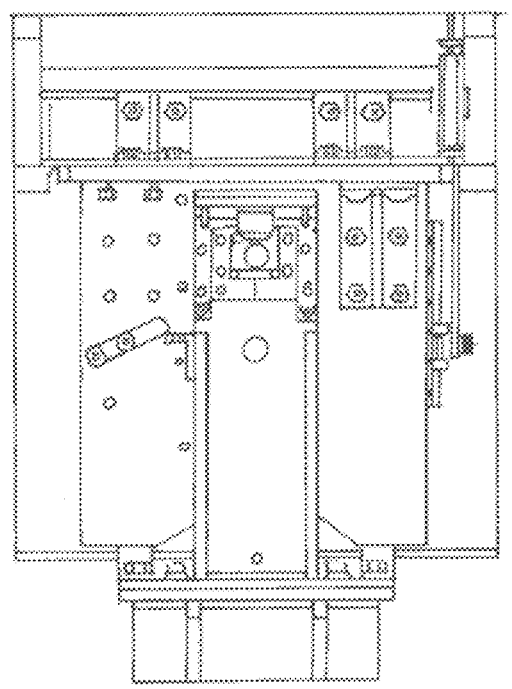
FIG. 15B is a diagram illustrating a bottom view of a smart docking module, comprising an active docking module and a passive docking module, as shown in FIG. 15A, wherein the active docking module, as shown in FIG. 6C, has engaged, docked, and locked with the passive docking module, in accordance with an embodiment of the present disclosure.

Referring to FIG. 15B, this diagram illustrates, in a bottom view, the smart docking module D, comprising the active docking module 310 and the passive docking module 320, as shown in FIG. 15A, wherein the active docking module 310, as shown in FIG. 6C, has engaged, docked, and locked with the passive docking module 320, in accordance with an embodiment of the present disclosure. If the bed 20 is determined to be in an extended position, an active docking latch 315 facilitates retention of the pins 322 in the slot 312, whereby undocking of the medical transporter apparatus A is prevented. As described in relation to FIG. 15A, the cam cable 317 is operably coupled with the interlock cam system 360 and actuates a dock interlock lever 313 which, in turn, actuates the active docking latch 315. Docking of the medical transporter apparatus A with the imaging apparatus I effects a tension in the cam cable 317 via the interlock cam system 360, thereby actuating the active docking latch 315 in relation to the interlocking feature 90 comprising the arm 91 and the stops 92.

Figure 15C:
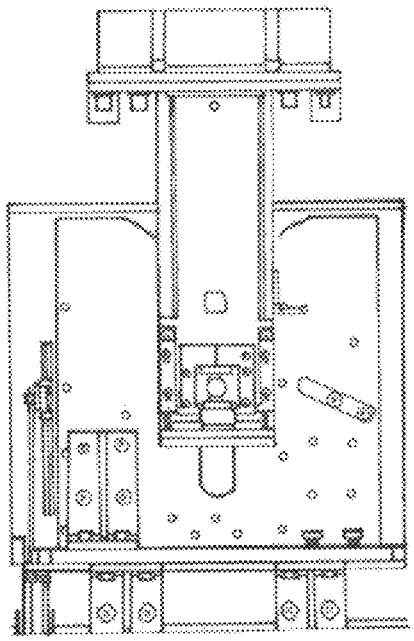
FIG. 15C is a diagram illustrating a bottom view of a smart docking module, comprising an active docking module and a passive docking module, wherein the active docking module, as shown in FIGS. 6D and 15A, is unlocking, disengaging, and undocking in relation to the passive docking module, in accordance with an embodiment of the present disclosure.

Referring to FIG. 15C, this diagram illustrates, in a bottom view, the smart docking module D, comprising the active docking module 310 and the passive docking module 320, wherein the active docking module 310, as shown in FIGS. 6D and 15A, is unlocking, disengaging, and undocking in relation to the passive docking module 320, in accordance with an embodiment of the present disclosure. When the active docking module 310 is determined to be "undocked" in relation to the passive docking module 320, the bed 20 is determined to be in a "transport" position. The passive docking module 320 comprises a forward section 320$f$ and an aft section 320$a$. The active docking module 310 comprises a dock interlock lever 313 operably coupled with the active docking cable 318. The forward section 320$f$ comprises an actuator 320$b$ configured to engage and disengage in relation to the dock interlock lever 313. The active docking cable 318 is operably coupled with the cam cable 317. When undocking the active docking module 310 from the passive docking module 320, actuator 320$b$ disengages the dock interlock lever 313, whereby the dock interlock lever 313 rotates clockwise, whereby tension in the cam cable 317 is released, whereby the cam 361 is returned to its original position, whereby the bed 20 is locked in relation to the table T, and whereby the bed 20 is constrained from translating in relation to the table T.

Figure 15D:
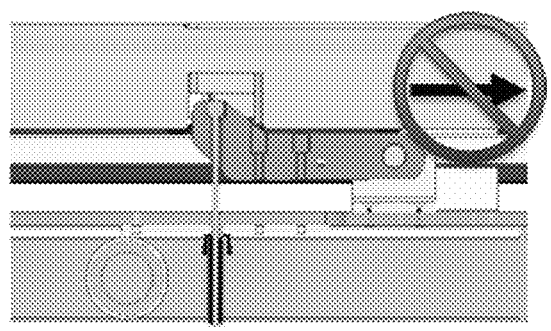
FIG. 15D is a diagram illustrating a cross-sectional side view of the interlock cam system, wherein tension in the cam cable is released, as shown in FIG. 15C, whereby the cam is returned to its original position, whereby the bed is locked in relation to the table, and whereby the bed is constrained from translating in relation to the table, in accordance with an embodiment of the present disclosure.

Referring to FIG. 15D, this diagram illustrates, in a cross-sectional side view, the interlock cam system 360, wherein tension in the cam cable 317 is released, as shown in FIG. 15C, whereby the cam 361 is returned to its original position, where the bed 20 is locked in relation to the table T, and whereby the bed 20 is constrained from translating in relation to the table T, in accordance with an embodiment of the present disclosure.

Figure 15E:
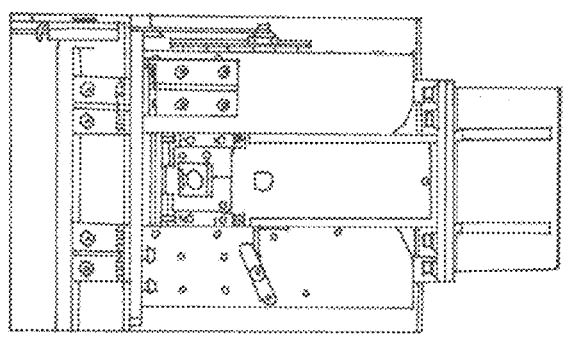
FIG. 15E is a diagram illustrating a bottom view of a smart docking module, comprising an active docking module and a passive docking module wherein the active docking module, as shown in FIGS. 6C and 15B, is engaged, docked, and locked in relation to the passive docking module, in accordance with an embodiment of the present disclosure.

Referring to FIG. 15E, this diagram this diagram illustrates, in a bottom view, the smart docking module D, comprising the active docking module 310 and the passive docking module 320, wherein the active docking module 310, as shown in FIGS. 6C and 15B, is engaged, docked, and locked in relation to the passive docking module 320, in accordance with an embodiment of the present disclosure. When the active docking module 310 is determined to be "docked" in relation to the passive docking module 320, the bed 20 is determined to be in a "scanning" position. The passive docking module 320 comprises a forward section 320$f$ and an aft section 320$a$. The active docking module 310 comprises a dock interlock lever 313 operably coupled with the active docking cable 318. The forward section 320$f$ comprises an actuator 320$b$ configured to engage and disengage in relation to the dock interlock lever 313. The active docking cable 318 is operably coupled with the cam cable 317. When undocking the active docking module 310 from the passive docking module 320, actuator 320$b$ engages the dock interlock lever 313, whereby the dock interlock lever 313 rotates counter-clockwise, whereby the cam cable 317 is tensioned, whereby the cam 361 is actuated from its original position, whereby the bed 20 is unlocked in relation to the table T, and whereby the bed 20 is enabled for translating in relation to the table T.

Figure 15F:
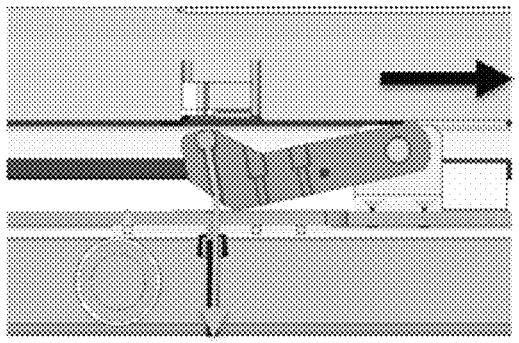
FIG. 15F is a diagram illustrating a cross-sectional side view of the interlock cam system, wherein the cam cable is tensioned, as shown in FIG. 15E, whereby the cam is returned to its original position, whereby the bed is unlocked in relation to the table, and whereby the bed is enabled for translating in relation to the table, in accordance with an embodiment of the present disclosure.

Referring to FIG. 15F, this diagram illustrates, in a cross-sectional side view, the interlock cam system 360, wherein the cam cable 317 is tensioned, as shown in FIG. 15E, whereby the cam 361 is returned to its original position, wherein the bed 20 is unlocked in relation to the table T, and whereby the bed 20 is enabled for translating in relation to the table T, in accordance with an embodiment of the present disclosure.

Figure 15G:
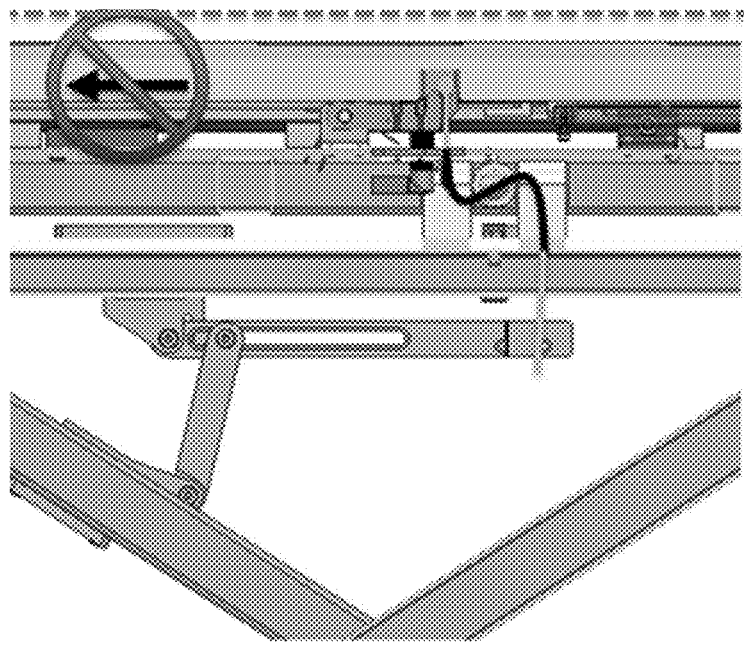
FIG. 15G is a diagram illustrating a cross-sectional side view of the interlock cam system interacting with the bed, the table, the motor-and-rail system, and the lifting mechanism, wherein tension in the cam cable is released, as shown in FIG. 15C, whereby the bed is constrained from translating in relation to the table, e.g., for a "transport" mode, in accordance with an embodiment of the present disclosure.

Referring to FIG. 15G, this diagram illustrates, in a cross-sectional side view, the interlock cam system 360 interacting with the bed 20, the table T, the motor-and-rail system 40, and the lifting mechanism 45, wherein tension in the cable 317 is released, as shown in FIG. 15C, wherein the cam cable 317 is operably coupled with the lifting mechanism 45, whereby the cam 361 is returned to its original position, whereby the lifting mechanism 45 is locked, whereby the bed 20 is locked in relation to the table T, and whereby the bed 20 is constrained from translating in relation to the table T, e.g., for a "transport" mode, in accordance with an embodiment of the present disclosure.

Figure 15H:
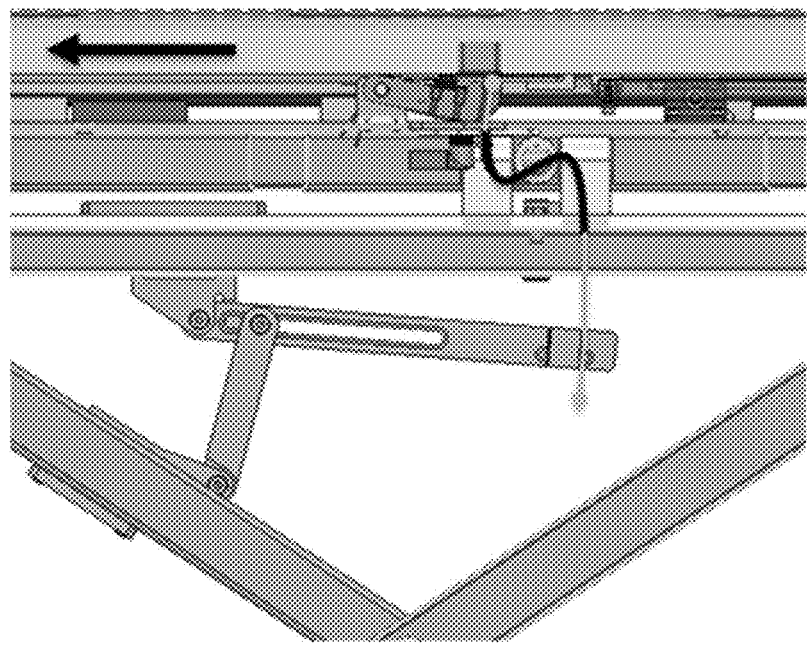
FIG. 15H is a diagram illustrating a cross-sectional side view of the interlock cam system interacting with the bed, the table, the motor-and-rail system, and the lifting mechanism, wherein tension in the cam cable is applied, as shown in FIG. 15E, whereby the bed is enabled for translating in relation to the table, e.g., for a "scanning" mode, in accordance with an embodiment of the present disclosure.

Referring to FIG. 15H, this diagram illustrates, in a cross-sectional side view, the interlock cam system 360 interacting with the bed 20, the table T, the motor-and-rail system 40, and the lifting mechanism 45, wherein tension in the cam cable 317 is applied, as shown in FIG. 15E, whereby the cam 361 is rotated from its original position, whereby the bed 20 is unlocked in relation to the table T, whereby the bed 20 is adjustable via the lifting mechanism 45 to a desired or requisite scanning height $h_s$, and whereby the bed 20 is enabled for translating in relation to the table T, e.g., for a "scanning" mode, in accordance with an embodiment of the present disclosure.

Figure 15I:
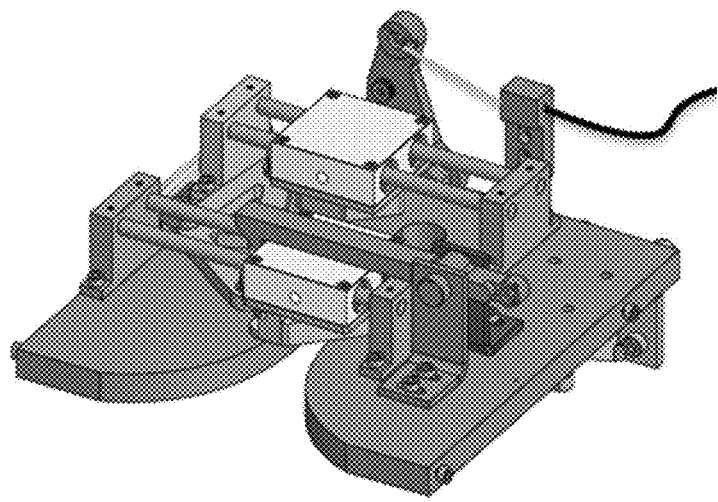
FIG. 15I is a diagram illustrating a perspective view of the active docking module of the smart docking module, wherein the active docking module provides input from the interlock cam system, as shown in FIG. 15D, that effectively actuates the latching mechanism, as shown in FIG. 7A, via a latching cable, in accordance with an embodiment of the present disclosure.

Referring to FIG. 15I, this diagram illustrates, in a perspective view, the active docking module 310 of the smart docking module D, in accordance with an embodiment of the present disclosure. The active docking module 310 provides input from the interlock cam system 360, as shown in FIG. 15D, that effectively actuates the latching mechanism 350, as shown in FIG. 7A, via a latching cable 330. When the active docking module 310 is docked and locked in relation to the passive docking module 320, tension in the latching cable 330 is released, whereby bed latches 351 disengage at least one patient positioner coupler 25$c$ of the patient positioner 25 (FIG. 15J).

Figure 15J:
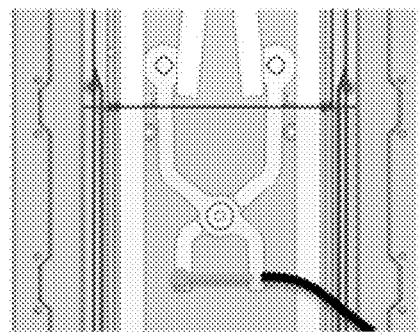
FIG. 15J is a diagram illustrating a top view of the latching mechanism, receiving input from the active docking module, as shown in FIG. 15I, in accordance with an embodiment of the present disclosure.

Referring to FIG. 15J, this diagram illustrates, in a perspective view, the latching mechanism 350, receiving input from the active docking module 310, as shown in FIG. 15I, in accordance with an embodiment of the present disclosure. By example only, the at least one bed latch 351 comprises a pair of bed latches 351. The latching cable 330 is operably coupled with a pair of rotatable latching actuator arms 354, whereby the pair of bed latches 351 may engage or disengage at least one patient positioner coupler 25*c* of the patient positioner 25. For example, each bed latch 351 comprises a raised cylindrical portion 351*c* shown as disengaged in relation to a surface 25*s* of the coupler 25*c*. An alternative latching configuration is shown in FIG. 7A.

Figure 15K:
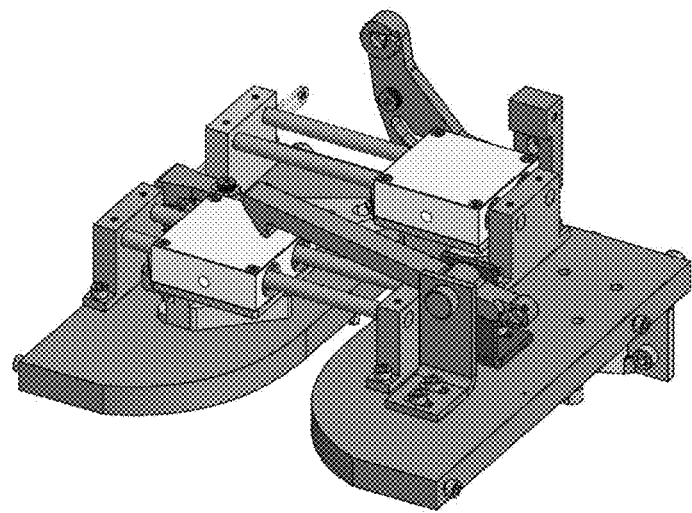
FIG. 15K is a diagram illustrating a perspective view of the active docking module of the smart docking module, wherein the active docking module provides input from the interlock cam system, as shown in FIG. 15F, that effectively actuates the latching mechanism, as shown in FIG. 7A, via the latching cable, as shown in FIG. 15I, in accordance with an embodiment of the present disclosure.

Referring to FIG. 15K, this diagram illustrates, in a perspective view, the active docking module 310 of the smart docking module D, in accordance with an embodiment of the present disclosure. The active docking module 310 provides input from the interlock cam system 360, as shown in FIG. 15F, that effectively actuates the latching mechanism 350, as shown in FIG. 7A, via the latching cable 330, as shown in FIG. 15I. When the active docking module 310 is unlocked and undocked in relation to the passive docking module 320, tension in the latching cable 330 is applied, whereby the bed latches 351 engage the at least one patient positioner coupler 25*c* of the patient positioner 25 (FIG. 15J).

Figure 15L:
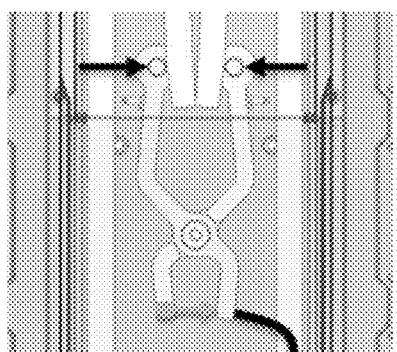
FIG. 15L is a diagram illustrating a top view of the latching mechanism, receiving input from the active docking module, as shown in FIG. 15K, whereby the pair of latches disengage the at least one patient positioner coupler of the patient positioner, in accordance with an embodiment of the present disclosure.

Referring to FIG. 15L, this diagram illustrates, in a top view, the latching mechanism 350, receiving input from the active docking module 310, as shown in FIG. 15K, in accordance with an embodiment of the present disclosure. By example only, the at least one bed latch 351 comprises a pair of bed latches 351. The latching cable 330 is operably coupled with the pair of rotatable latching actuator arms 354, whereby the pair of bed latches 351 disengage the at least one patient positioner coupler 25*c* of the patient positioner 25. For example, each bed latch 351, comprising the raised cylindrical portion 351*c* is shown as engaging the surface 25*s* of the coupler 25*c*, e.g., in a direction indicated by arrows 97.

Figure 16:
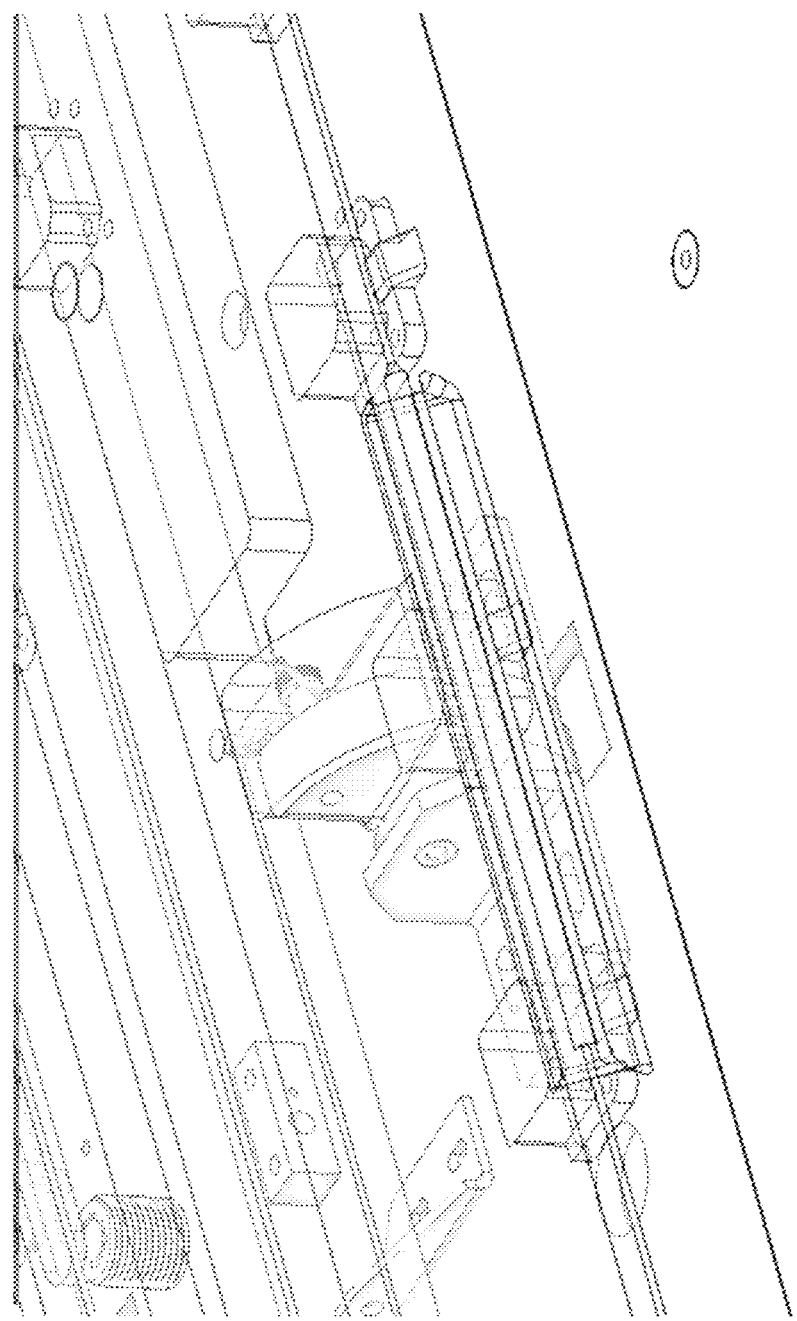
FIG. 16 is a diagram illustrating an internal view of other components of the interlock cam system, as shown in FIGS. 11C and 11D, in accordance with an embodiment of the present disclosure.

Referring to FIG. 16, this diagram illustrates, in an internal view, other components of the interlock cam system 360, as shown in FIGS. 11C and 11D, in accordance with an embodiment of the present disclosure. When the bed 20 is determined to be in the "transport" position, the bed 20 is locked in relation to the table T by the cam 361. The cam cable 317 that is tensioned by the dock interlock lever 313 which rotates the cam 361 and passivates the locked state, thereby releasing the bed 20 for translation in relation to the table T.

Figure 17:
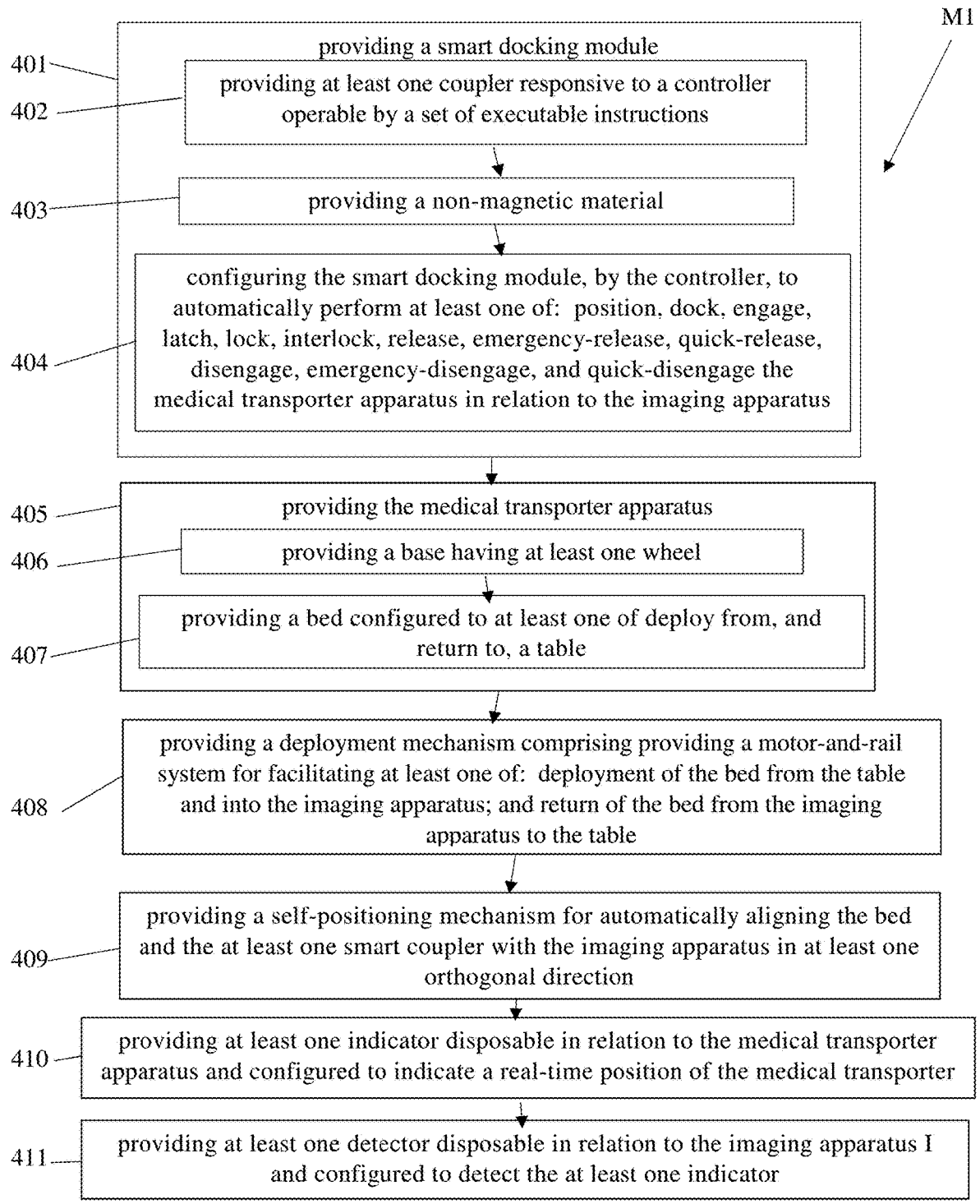
FIG. 17 is a flow diagram illustrating a method of fabricating a smart system for coupling a medical transporter apparatus with an imaging apparatus, in accordance with an embodiment of the present disclosure.

Referring to FIG. 17, this flow diagram illustrates a method M1 of fabricating a smart system S for coupling a medical transporter apparatus A with an imaging apparatus I, in accordance with an embodiment of the present disclosure. The method M1 comprises: providing a smart docking module D, as indicated by block 401, providing the smart docking module D comprising: providing at least one coupler responsive to a controller operable by a set of executable instructions, as indicated by block 402, providing a non-magnetic material, as indicated by block 403; and configuring the smart docking module D, by the controller, to automatically perform at least one of: position, dock, engage, latch, lock, interlock, release, emergency-release, quick-release, disengage, emergency-disengage, and quick-disengage the medical transporter apparatus A in relation to the imaging apparatus I, as indicated by block 404. Providing the at least one coupler, as indicated by block 402, comprises providing at least one of: at least one latch, at least one bed latch, and at least one active docking latch.

Still referring to FIG. 17, in the method M1, the medical transporter apparatus A is configured to accommodate a patient and comprises at least one of: a magnetic imaging table, a surgery table, a cart, a bed, a frame, a mattress, a gurney, and a stretcher. The imaging apparatus I comprises at least one of a magnetic resonance imaging machine, a magnetic resonance angiography machine, a nuclear magnetic resonance machine, and any other type of magnetic imaging machine. The controller comprises at least one of: a computer, a processor, a processing unit, a power source, a memory device, and a safety device.

Still referring to FIG. 17, the method M1 further comprises providing the medical transporter apparatus A, as indicated by block 405, providing the medical transporter T comprising: providing a base B having at least one wheel W, as indicated by block 406; providing a bed 20 configured to at least one of deploy from, and return to, a table T, as indicated by block 407; providing a deployment mechanism comprising providing a motor-and-rail system 40 for facilitating at least one of: deployment of the bed 20 from the table T and into the imaging apparatus I; and return of the bed 20 from the imaging apparatus to the table T, as indicated by block 408; and providing a self-positioning mechanism for automatically aligning the bed 20 and the at least one smart coupler with the imaging apparatus I in at least one orthogonal direction, as indicated by block 409.

Still referring to FIG. 17, the method M1 further comprises: providing at least one indicator disposable in relation to the medical transporter apparatus A and configured to indicate a real-time position of the medical transporter apparatus A, as indicated by block 410; and providing at least one detector disposable in relation to the imaging apparatus I and configured to detect the at least one indicator, as indicated by block 411. Providing the at least one indicator, as indicated by block 410, comprises providing at least one of: at least one tracking marker, at least one fluorescent tracking marker, and at least one infrared tracking marker. Providing the at least one detector, as indicated by block 411, comprises providing at least one of: at least one sensor, at least one optical sensor, at least one photosensor, at least one photo-detector, at least one electric eye, at least one infrared sensor, and at least one photo-interrupter.

Still referring to FIG. 17, the method M1 further comprises: providing a user interface comprising providing at least one of: a foot pedal, a handle, a joystick, and a graphic user interface, the user interface facilitating at least one of activation, control, manually positioning, and manually overriding operation of at least one of: the at least one coupler, the deployment mechanism, and the self-positioning mechanism, as indicated by block 411, wherein providing the self-positioning mechanism, as indicated by block 409, comprises providing at least one of: a patient positioner, a belt-drive system, and a cable carrier system.

Figure 18:
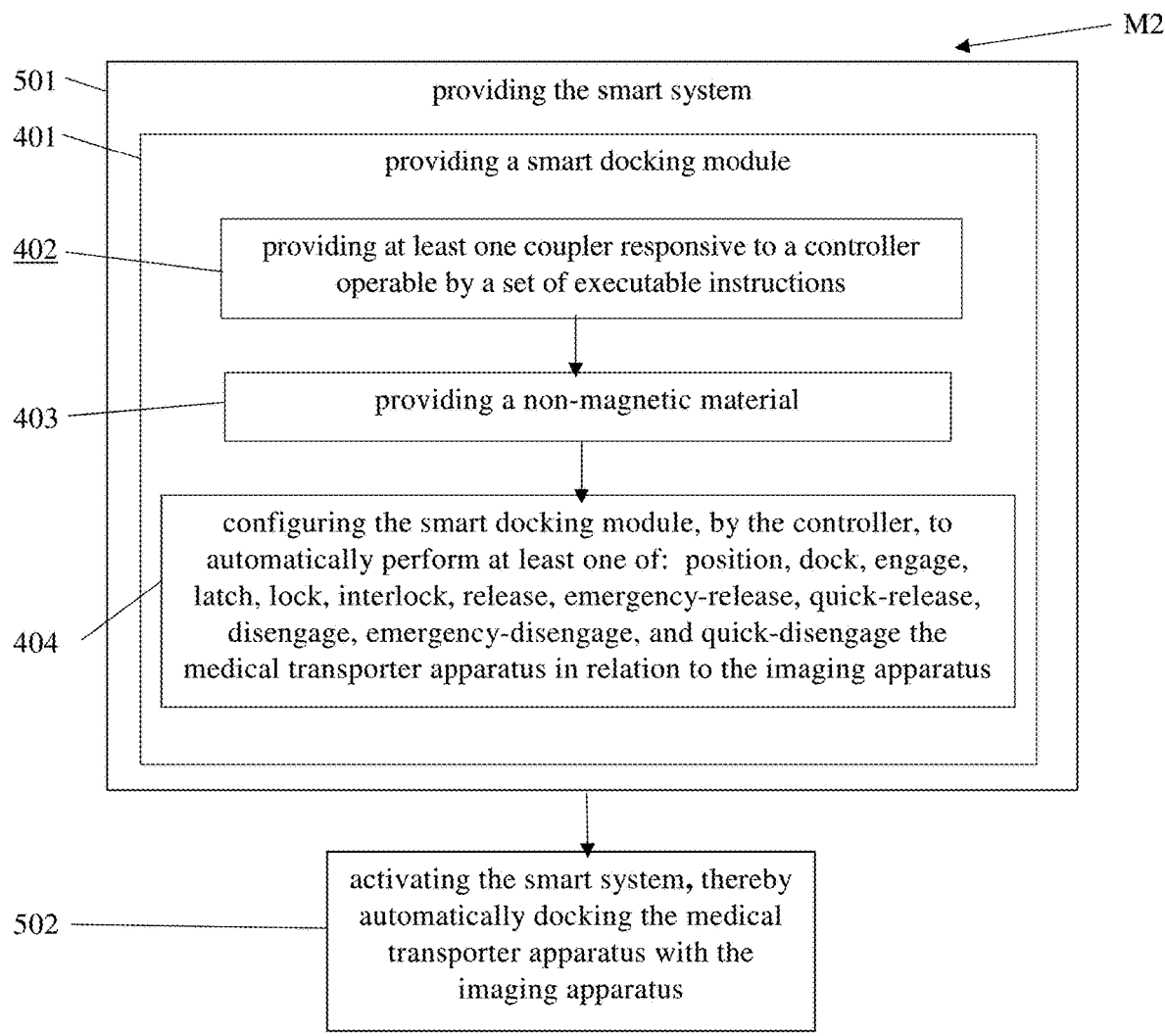
FIG. 18 is a flow diagram illustrating a method of coupling a medical transporter apparatus with an imaging apparatus, by way of a smart system, in accordance with an embodiment of the present disclosure.

Referring to FIG. 18, this flow diagram illustrates a method M2 of coupling a medical transporter apparatus A with an imaging apparatus I, by way of a smart system S, comprising a smart docking module D, in accordance with an embodiment of the present disclosure. The method M2 comprises: providing the smart system S, as indicated by block 501, providing the smart system S comprising: providing a smart docking module D, as indicated by block 401, providing the smart docking module D comprising: providing at least one coupler responsive to a controller operable by a set of executable instructions, as indicated by block 402, providing a non-magnetic material, as indicated by block 403; and configuring the smart docking module D, by the controller, to automatically perform at least one of: position, dock, engage, latch, lock, interlock, release, emergency-release, quick-release, disengage, emergency-disengage, and quick-disengage the medical transporter apparatus A in relation to the imaging apparatus I, as indicated by block 404; and activating the smart system S, as indicated by block 501, thereby automatically docking the medical transporter apparatus A with the imaging apparatus I.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become obvious to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the present disclosure.

INDUSTRIAL APPLICABILITY

Generally, the present disclosure industrially applies to patient transport apparatuses and methods. More particularly, the present disclosure industrially applies to patient transport apparatuses and methods for use with MRI machines. Even more particularly, the present disclosure industrially applies to patient transport apparatuses and methods that are interfaceable with MRI machines.

What is claimed:

1. A smart system for coupling a medical transporter apparatus with an imaging apparatus, comprising:
    a smart docking module, the smart docking module comprising at least one coupler responsive to a controller operable by a set of executable instructions, the smart docking module comprising a non-magnetic material and the smart docking module configured, by the controller, to automatically perform at least one of: position, dock, engage, latch, lock, interlock, release, emergency-release, quick-release, disengage, emergency-disengage, and quick-disengage the medical transporter apparatus in relation to the imaging apparatus;
    the medical transporter apparatus, the medical transporter apparatus comprising a table, a bed operably coupled with the table, a base having at least one wheel, and a lift portion, the lift portion coupling the table with the base, and the lift portion configured to adjust elevation of the table in relation to the base;
    a deployment mechanism, the deployment mechanism comprising a motor-and-rail system for facilitating at least one of: deployment of the bed from the table and into a scanning volume of the imaging apparatus, return of the bed from the scanning volume of the imaging apparatus to the table, deployment of an active docking module of the smart docking module from the base to a passive docking module coupled with a receiver portion of the imaging apparatus, and return of the smart docking module to the base from the passive docking module coupled with the receiver portion of the imaging apparatus; and
    a self-positioning mechanism for automatically aligning the bed with the scanning volume of the imaging apparatus and the at least one smart coupler with the receiver portion of the imaging apparatus in at least one orthogonal direction, the self-positioning mechanism comprising a patient positioner, a belt-drive system, and a cable carrier system.

2. The smart system of claim 1, wherein the medical transporter apparatus is configured to accommodate a patient and comprises at least one of: a magnetic imaging table, a surgery table, a cart, a bed, a frame, a mattress, a gurney, and a stretcher.

3. The smart system of claim 1, wherein the imaging apparatus comprises at least one of a magnetic resonance imaging machine, a magnetic resonance angiography machine, a nuclear magnetic resonance machine, and any other type of magnetic imaging machine.

4. The smart system of claim 1, wherein the controller comprises at least one of: a computer, a processor, a processing unit, a power source, a memory device, and a safety device.

5. The system of claim 1, wherein the at least one coupler comprises at least one of: at least one latch, at least one bed latch, and at least one active docking latch.

6. The smart system of claim 1, further comprising:
    at least one indicator disposable in relation to the medical transporter apparatus and configured to indicate a real-time position of the medical transporter apparatus; and
    at least one detector disposable in relation to the imaging apparatus and configured to detect the at least one indicator.

7. The smart system of claim 6,
    wherein the at least one indicator comprises at least one of: at least one tracking marker, at least one fluorescent tracking marker, and at least one infrared tracking marker, and
    wherein the at least one detector comprises at least one of: at least one sensor, at least one optical sensor, at least one photo-sensor, at least one photo-detector, at least one electric eye, at least one infrared sensor, and at least one photo-interrupter.

8. The smart system of claim 1, further comprising a user interface, the user interface comprising at least one of: a foot pedal, a handle, a joystick, and a graphic user interface, the user interface facilitating at least one of activation, control, and manual override of at least one of: the at least one coupler, the deployment mechanism, and the self-positioning mechanism.

9. A method of fabricating a smart system for coupling a medical transporter apparatus with an imaging apparatus, comprising:
    providing a smart docking module, providing the smart docking module comprising providing at least one coupler responsive to a controller operable by a set of executable instructions, providing the smart docking module comprising providing a non-magnetic material, and providing the smart docking module comprising configuring the smart docking module, by the controller, to automatically perform at least one of: position, dock, engage, latch, lock, interlock, release, emergency-release, quick-release, disengage, emergency-disengage, and quick-disengage the medical transporter apparatus in relation to the imaging apparatus;

providing the medical transporter apparatus, providing the medical transporter apparatus comprising providing: a table, a bed operably coupled with the table, a base having at least one wheel, and a lift portion, providing the lift portion comprising coupling the table with the base, and providing the lift portion comprising configuring the lift portion to adjust elevation of the table in relation to the base;

providing a deployment mechanism, providing the deployment mechanism comprising providing a motor-and-rail system for facilitating at least one of: deployment of the bed from the table and into a scanning volume of the imaging apparatus; return of the bed from the scanning volume of the imaging apparatus to the table; deployment of an active docking module of the smart docking module from the base to a passive docking module coupled with a receiver portion of the imaging apparatus; and return of the smart docking module to the base from the passive docking module coupled with the receiver portion of the imaging apparatus; and providing a self-positioning mechanism for automatically aligning the bed with the scanning volume of the imaging apparatus and the at least one smart coupler with the receiver portion of the imaging apparatus in at least one orthogonal direction, providing the self-positioning mechanism comprising providing: a patient positioner, a belt-drive system, and a cable carrier system.

10. The method of claim 9, wherein the medical transporter apparatus is configured to accommodate a patient and comprises at least one of: a magnetic imaging table, a surgery table, a cart, a bed, a frame, a mattress, a gurney, and a stretcher.

11. The method of claim 9, wherein the imaging apparatus comprises at least one of a magnetic resonance imaging machine, a magnetic resonance angiography machine, a nuclear magnetic resonance machine, and any other type of magnetic imaging machine.

12. The method of claim 9, wherein the controller comprises at least one of: a computer, a processor, a processing unit, a power source, a memory device, and a safety device.

13. The method of claim 9, wherein providing the at least one coupler comprises providing at least one of: at least one latch, at least one bed latch, and at least one active docking latch.

14. The method of claim 9, further comprising:
providing at least one indicator disposable in relation to the medical transporter apparatus and configured to indicate a real-time position of the medical transporter; and
providing at least one detector disposable in relation to the imaging apparatus and configured to detect the at least one indicator.

15. The method of claim 14,
wherein providing the at least one indicator comprises providing at least one of: at least one tracking marker, at least one fluorescent tracking marker, and at least one infrared tracking marker, and
wherein providing the at least one detector comprises providing at least one of: at least one sensor, at least one optical sensor, at least one photo-sensor, at least one photo-detector, at least one electric eye, at least one infrared sensor, and at least one photo-interrupter.

16. The method of claim 9, further comprising providing a user interface comprising providing at least one of: a foot pedal, a handle, a joystick, and a graphic user interface, providing the user interface comprising configuring the user interface to facilitate at least one of activation, control, manually positioning, and manually overriding operation of at least one of: the at least one coupler and the deployment mechanism.

17. A method of coupling a medical transporter apparatus with an imaging apparatus by way of a smart system, comprising:
providing the smart system, providing the smart system comprising: providing a smart docking module comprising providing at least one coupler responsive to a controller operable by a set of executable instructions, providing the smart docking module comprising providing a non-magnetic material, and providing the smart docking module comprising configuring the smart docking module, by the controller, to automatically perform at least one of: position, dock, engage, latch, lock, interlock, release, emergency-release, quick-release, disengage, emergency-disengage, and quick-disengage the medical transporter apparatus in relation to the imaging apparatus;

providing the medical transporter apparatus, providing the medical transporter apparatus comprising providing: a table, a bed operably coupled with the table, a base having at least one wheel, and a lift portion, providing the lift portion comprising coupling the table with the base, and providing the lift portion comprising configuring the lift portion to adjust elevation of the table in relation to the base;

providing a deployment mechanism, providing the deployment mechanism comprising providing a motor-and-rail system for facilitating at least one of: deployment of the bed from the table and into a scanning volume of the imaging apparatus; return of the bed from the scanning volume of the imaging apparatus to the table; deployment of an active docking module of the smart docking module from the base to a passive docking module coupled with a receiver portion of the imaging apparatus; and return of the smart docking module to the base from the passive docking module coupled with the receiver portion of the imaging apparatus; and providing a self-positioning mechanism for automatically aligning the bed with the scanning volume of the imaging apparatus and the at least one smart coupler with the receiver portion of the imaging apparatus in at least one orthogonal direction, providing the self-positioning mechanism comprising providing: a patient positioner, a belt-drive system, and a cable carrier system; and activating the smart system, thereby automatically docking the medical transporter apparatus with the imaging apparatus.

* * * * *